US008945527B2

(12) United States Patent
DeSimone et al.

(10) Patent No.: US 8,945,527 B2
(45) Date of Patent: Feb. 3, 2015

(54) DEGRADABLE COMPOUNDS AND METHODS OF USE THEREOF, PARTICULARLY WITH PARTICLE REPLICATION IN NON-WETTING TEMPLATES

(75) Inventors: Joseph DeSimone, Chapel Hill, NC (US); Matthew Parrott, Carrboro, NC (US); Andrew Murphy, Cary, NC (US); Robby A. Petros, Denton, TX (US)

(73) Assignees: The University of North Carolina at Chapel Hill, Chapel Hill, NC (US); Liquidia Technologies, Inc., Durham, NC (US)

( * ) Notice: Subject to any disclaimer, the term of this patent is extended or adjusted under 35 U.S.C. 154(b) by 497 days.

(21) Appl. No.: 12/989,315

(22) PCT Filed: Apr. 24, 2009

(86) PCT No.: PCT/US2009/041652
§ 371 (c)(1),
(2), (4) Date: Feb. 9, 2011

(87) PCT Pub. No.: WO2009/132265
PCT Pub. Date: Oct. 29, 2009

(65) Prior Publication Data
US 2011/0123446 A1 May 26, 2011

Related U.S. Application Data

(60) Provisional application No. 61/048,032, filed on Apr. 25, 2008.

(51) Int. Cl.
A61K 31/74 (2006.01)
C07F 7/18 (2006.01)

(52) U.S. Cl.
CPC ..................... *C07F 7/184* (2013.01)
USPC ...................................... 424/78.08

(58) Field of Classification Search
None
See application file for complete search history.

(56) References Cited

U.S. PATENT DOCUMENTS

| 4,904,563 | A | 2/1990 | Aoai et al. | |
|---|---|---|---|---|
| 5,827,925 | A | 10/1998 | Tremont et al. | |
| 6,030,959 | A | 2/2000 | Tremont et al. | |
| 6,121,404 | A | 9/2000 | Liles | |
| 6,413,945 | B1 | 7/2002 | Tremont et al. | |
| 6,569,458 | B1 | 5/2003 | Gombotz et al. | |
| 2008/0076882 | A1* | 3/2008 | Ozai | 525/387 |
| 2009/0317335 | A1 | 12/2009 | Lin et al. | |
| 2011/0135571 | A1 | 6/2011 | Lin et al. | |

FOREIGN PATENT DOCUMENTS

| CH | 569029 | 11/1975 |
|---|---|---|
| DE | 1133133 | 7/1962 |
| DE | 2044888 | 3/1971 |
| EP | 0525392 | 2/1993 |
| EP | 0754691 | 1/1997 |
| EP | 1201672 | 5/2002 |
| JP | 5-255348 A | 10/1993 |
| WO | WO-2009/132265 A2 | 10/2009 |

OTHER PUBLICATIONS

Gratton et al., J. Control. Release (2007) 121(1-2):10-18.*
Themistou, E., and C.S. Patrickios, "Synthesis and Characterization of Star Polymers and Cross-Linked Star Polymer Model Networks Containing a Novel, Silicon-Based, Hydrolyzable Cross-Linker," *Macromolecules*, 2004, pp. 6734-6743, vol. 37.
"Silicon Compounds," Gelest, XP002533455, 2004, pp. 215-386.
Chen, Yiwang, et al., "Preparation of Hollow Silica Nanospheres by Surface-Initiated Atom Transfer Radical Polymerization on Polymer Latex Templates," *Advanced Functional Materials*, Jan. 2005, pp. 113-117, vol. 15(1), Wiley-VCH Verlag GmbH & Co. KGaA, Weinheim.
Chung, et al., "Photopolymerization and curing shrinkage of silicon-containing multifunctional methacrylates", *Journal of Materials Science Letters*, 2002, pp. 1093-1095, vol. 21.
Furusawa, et al., "New sila-analogues of cyclic nucleotides, 3', 5' -O-silanediyl nucleosides", *Tetrahedron Letters*, 1985, pp. 887-890, vol. 26, No. 7.
Garner, Philip et al., "Use of Silicon-Based Tethers to Control Diastereofacial Selectivity in Azomethine Ylide Cycloadditions", *Journal of Organic Chemistry*, Jan. 1, 1997, pp. 493-498, vol. 62.
Kumagai, et al., "Cyclic di-t-butylsilylenediyl ether group as a convenient protective group for the glycoconjugate synthesis", *Tetrahedron Letters*, 2001, pp. 1953-1956, vol. 42.
Mahkam, M. et al., "PH-sensitive hydrogel containing Acetaminophen silyl ethers for colon-specific drug delivery", *Designed Monomers and Polymers*, VSP, Utrecht, NL, Nov. 1, 2006, pp. 607-615, vol. 9, No. 6.
Parrott, Matthew C., et al., "Tunable Bifunctional Silyl Ether Cross-Linkers for the Design of Acid-Sensitive Biomaterials", *Journal of the American Chemical Society*, Nov. 24, 2010, pp. 17928-17932, vol. 132, No. 50.

(Continued)

*Primary Examiner* — Michael G Hartley
*Assistant Examiner* — Robert Cabral
(74) *Attorney, Agent, or Firm* — Alston & Bird LLP

(57) ABSTRACT

The present invention provides compounds that will degrade under specified conditions, methods of using such compounds, and compositions comprising such compounds. The degradable compounds of the invention may be characterized by the labile —Si-A-C— groups present in the compounds (A representing an atom, such as O, N, or S, or a group, such as C=O). The compounds may be incorporated into a composition that further may include a polymeric matrix and/or a cargo component. A wide variety of cargo components may also be used in the present invention. In particular embodiments, the cargo component comprises a drug or other therapeutic agent. Accordingly, the invention particularly provides pharmaceutical formulations and methods of delivering a drug or other therapeutic material.

24 Claims, 5 Drawing Sheets

(56) References Cited

OTHER PUBLICATIONS

Perkins, W.E., et al.., "Polymer Delivery of the Active Isomer of Misoprostol: A Solution to the Intestinal Side Effect Problem," *The Journal of Pharmacology and Experimental Therapeutics*, Dec. 13, 1993, pp. 151-156, vol. 269(1), The American Society for Pharmacology and Experimental Therapeutics.

Shea, K.J. et al., "Pericyclic Umpolung. Reversal of Regioselectivity in the Diels-Alder Reaction", *Tetrahedron Letters*, 1991, pp. 2715-2718, vol. 32, No. 24.

Tremont, S.J. et al., "Catalytic Functionalization of Polymers: A Novel Approach to Site Specific Delivery of Misoprostol to the Stomach", Journal of Medicinal Chemistry, Jan. 1, 1993, pp. 3087-3097, vol. 36, No. 21, American Chemical Society, US.

Trost, et al., "The di-t-butylsilylene protecting group for diols", *Tetrahedron Letters*, 1981, pp. 4999-5002, vol. 22, No. 50.

Burkhard, C., "The Reaction of Chlorosilanes with 2-Methoxyethanol," *Contribution from The Research Laboratory, General Electric Co.*, Jul. 13, 1949, pp. 106-107.

\* cited by examiner

DEGRADABLE COMPOUNDS AND METHODS OF USE THEREOF, PARTICULARLY WITH PARTICLE REPLICATION IN NON-WETTING TEMPLATES

CROSS REFERENCE TO RELATED APPLICATION

This application is a §371 U.S. National Stage of International Application No. PCT/US2009/041652, filed Apr. 24, 2009, which claims the benefit of U.S. Provisional Application Ser. No. 61/048,032, filed Apr. 25, 2008, the contents of which are herein incorporated by reference in their entirety.

STATEMENT OF GOVERNMENT SUPPORT

This invention was made with government support under CHE-9876674 awarded by the National Science Foundation and with government support under GM059299 and CA119343 awarded by the National Institutes of Health. The government has certain rights in the invention.

FIELD OF THE INVENTION

The present invention is directed to degradable compounds that may be used for delivery of a cargo component. More particularly, the degradable compounds may comprise a composition that degrades under specified conditions and that may release a component contained by the composition.

BACKGROUND OF THE INVENTION

Devices and methods for delivery of desired components to a site of interest remain a growing need. For example, a variety of methods and routes of administration have been developed to deliver pharmaceuticals, such as small molecular drugs and other biologically active compounds (e.g., peptides, hormones, proteins, and enzymes). Many routes of administration are known for delivering desired pharmaceuticals to a patient. As greater knowledge is learned regarding toxicity of drugs and the ability to elicit specific responses by delivery of a pharmaceutical only to a specific portion of the body, controlled release of pharmaceuticals after their administration has become a highly important area of research.

Gene therapy, for example, is a promising field; however, such therapy requires gene or polynucleotide transfer across the cell membrane and into the nucleus where the gene can be expressed. Many conventional drug delivery techniques simply cannot provide a delivery vehicle of sub-cellular dimensions that can effectively deliver specific materials to individual cells. The effectiveness of drugs and other compounds can also be increased by target specific delivery, and the use of micro- or nano-sized delivery devices can be particularly beneficial to increase drug activity while actually reducing the overall concentration of drug delivered. Accordingly, there is a need in the art for compounds and methods useful to facilitate delivery and release of desired compounds to a site of interest, particularly on a micro- or nano-size scale.

SUMMARY OF THE INVENTION

The present invention is directed to compounds that will degrade under specified conditions, methods of using such compounds, and compositions comprising such compounds. The degradable compounds of the invention may be characterized by the labile —Si-A-C— groups present in the compounds (A representing an atom, such as O, N, or S, or a group, such as C=O). The compounds are stable under defined conditions but are degradable under specified conditions, such as, for example, physiological temperature (e.g., about 37° C.) or acidic conditions. The compounds may be incorporated into a composition including a polymeric matrix and/or a cargo component. In certain embodiments, the polymeric matrix can be any material useful for forming discrete particles. Of course, depending upon the desired mode of delivery, the matrix material can comprise any number of materials useful for physically or chemically combining with the cargo component. In some embodiments, the degradable compound of the invention may be used as a crosslinker material, thus forming a part of the matrix material. In other embodiments, the matrix material may be substantially completely formed of the degradable compound. A wide variety of cargo components also may be used in the present invention. In particular embodiments, the cargo component comprises a drug or other therapeutic agent. Accordingly, the invention particularly provides methods of delivering a drug or other therapeutic material.

In one aspect, the invention is particularly directed to degradable compounds. According to certain embodiments, a degradable compound according to the invention may have a structure according to Formula (1a),

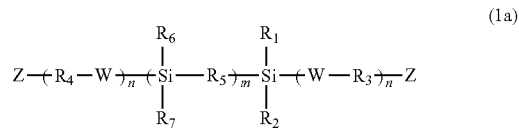

wherein:

W is O, NH, N—CH$_3$, SH, S—CH$_3$, or C(O)O;

R$_1$, R$_2$, R$_6$, and R$_7$ are the same or different and are optionally substituted straight or branched chain C$_1$-C$_6$ alkyl, alkenyl, or alkynyl; optionally substituted C$_3$-C$_6$ cycloalkyl, cycloalkenyl, or cycloalkynyl; optionally substituted phenyl or benzyl; or optionally substituted polyether or polyester;

R$_3$ and R$_4$ are the same or different and are optionally substituted straight or branched chain C$_1$-C$_{12}$ alkyl, alkenyl, or alkynyl; or optionally substituted polyether or polyester;

R$_5$ is (W)$_p$—Y—(W)$_p$;

Y is optionally substituted straight or branched chain C$_1$-C$_{12}$ alkyl, alkenyl, or alkynyl; or optionally substituted polyether or polyester;

p is 0 or 1;

each Z is independently a polymerizable group;

m is an integer from 0 to 6; and n is an integer from 0 to 30.

In other embodiments, the degradable compound may have the structure of Formula (1b),

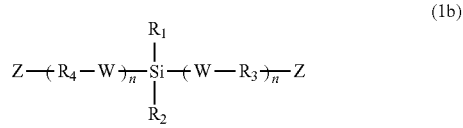

wherein:

W is O, NH, N—CH$_3$, SH, S—CH$_3$, or C(O)O;

R$_1$ and R$_2$ are the same or different and are optionally substituted straight or branched chain C$_1$-C$_6$ alkyl, alkenyl, or alkynyl; optionally substituted C$_3$-C$_6$ cycloalkyl, cycloalkenyl, or cycloalkynyl; optionally substituted phenyl or benzyl; or optionally substituted polyether or polyester;

$R_3$ and $R_4$ are the same or different and are optionally substituted straight or branched chain $C_1$-$C_{12}$ alkyl, alkenyl, or alkynyl; or optionally substituted polyether or polyester;

each Z is independently a polymerizable group;

m is an integer from 0 to 6; and n is an integer from 0 to 30.

According to specific embodiments, W may be O, $R_1$, $R_2$, $R_6$, and $R_7$ independently may be selected from the group consisting of ethyl, methyl, propyl, isopropyl, butyl, and tert-butyl, $R_3$ and $R_4$ independently may be selected from the group consisting of methyl, ethyl, and propyl, Z may be a group comprising a terminal C=C bond or a group comprising a C=O bond, Z may be a UV polymerizable group, and n may be an integer from 1 to 10.

The invention also provides methods of preparing the above compounds. In some embodiments, the method of preparation comprises reacting a functionalized silane compound with a functionalized organic compound. Preferably, at least one functional group on the reactants comprises an O atom, an N atom, an S atom, or a C=O group that may be directly bonded to the Si atom of the silane compound. In specific embodiments, the silane compound comprises organic substituents. Such substituents can be useful in the finally prepared degradable compounds for regulating degradation rate of the compound.

In another aspect, the present invention provides compositions comprising the degradable compounds of the invention. In certain embodiments, the compositions particularly may comprise a matrix material and a cargo component, which may be a drug, a therapeutic material, or any other compound capable of being physically or chemically combined with the matrix material. The matrix material may be at least partially formed using the degradable compounds of the invention, or the degradable material may be otherwise associated with the matrix material (e.g., attached to a surface of a particle formed from the matrix material). Thus, the composition provides for delivery and release of the cargo component through degradation of the composition.

In one embodiment, the invention provides a composition comprising a cargo component and a matrix material, the matrix material comprising a degradable compound having the structure of Formula (1a), as described above. In specific embodiments, the degradable compound may comprise about 0.1% to about 50% by weight of the matrix material, about 50% to about 99.9% by weight of the matrix material, or about 10% to about 90% by weight of the matrix material.

In some embodiments, the matrix material may be a co-polymer comprising the degradable compound and one or more co-monomers. In further embodiments, the matrix material may comprise one or more polymers cross-linked with the degradable compound. The composition also may comprise further components, such as a polymerization initiator (e.g., a photoinitiator). In other embodiments, the matrix material specifically may comprise a biodegradable polymer.

The cargo component may be associated with the matrix material via a variety of means. For example, the cargo component may be encapsulated by the matrix material, the cargo component may be physically blended with the matrix material, and/or the cargo component may be covalently bonded to one or more functional groups present on the matrix material. In one embodiment, the matrix material may be in the form of a particle having the degradable compound covalently bonded to one or more functional groups present on an exposed surface of the particle, and the cargo component may be attached to the particle via the degradable compound.

In certain embodiments, the composition of the invention may be provided in the form of discrete particles. Such discrete particles particularly may be prepared using particle replication in non-wetting templates (known as the PRINT™ process). Thus, the composition of the invention may be formed into discrete particles of micro- and nano-scale dimensions. Such particles may be administered directly to a site where it is desirable for the cargo component to be released. In some embodiments, the discrete particles may be incorporated into pharmaceutical formulations.

Accordingly, in certain embodiments, the invention may be directed to a particle comprising a degradable compound having the structure of Formula (1a), as described herein. The particle further may comprise a cargo component associated with the particle. Also, the particle may be a surface-activated particle. Specifically, the particle may have an exposed surface with a degradable compound according to the invention attached thereto and including a reactive group that makes the particle activated in that it is ready to receive a further component (e.g., a cargo component) that will covalently attach to the particle via the degradable compound.

A pharmaceutical formulation according to the invention may comprise a pharmaceutically acceptable carrier, a pharmaceutical material, and a degradable compound having the structure of Formula (1a), as described herein. In particular, the formulation may comprise a matrix material including the degradable compound. Still further, the matrix material may be in the form of a particle. In such embodiments, the pharmaceutical material may be associated with the particle (e.g., attached to an exposed surface of the particle via the degradable compound and/or at least partially encapsulated by the particle).

In other embodiments, a composition according to the invention may comprise a first particle type and a second particle type, each particle type comprising a matrix material and a cargo component, and the matrix material of at least one particle type comprising a degradable compound having the structure of Formula (1a), as described herein.

In particular embodiments, the composition can vary by altering various components of the particles. For example, the first particle type can different from the second particle type in one or more of the matrix material and the cargo component. Specifically, the polymeric makeup of the matrix material in each particle type may differ, and/or the cargo component used in each particle type may differ, and/or the degradable compound used in each particle type may differ.

In another aspect, the present thus also provides methods of treatment. The wide applicability of the degradable particles described above makes them particularly useful in treating a wide variety of conditions and diseases. Virtually any drug or therapeutic agent may be formed into the inventive, degradable particles. Accordingly, in certain embodiments, the invention provides methods of treating a patient comprising administering to the patient a composition according to the invention (particularly in the form of discrete particles). Preferably, the composition comprises a drug or therapeutic agent known to prevent, treat, cure, or ameliorate a disease or condition. Thus, in one embodiment, the method of the invention may comprise administering to a patient a composition comprising a pharmaceutical material, and a degradable compound having the structure of Formula (1a), as described herein.

BRIEF DESCRIPTION OF THE DRAWINGS

Figure 1:
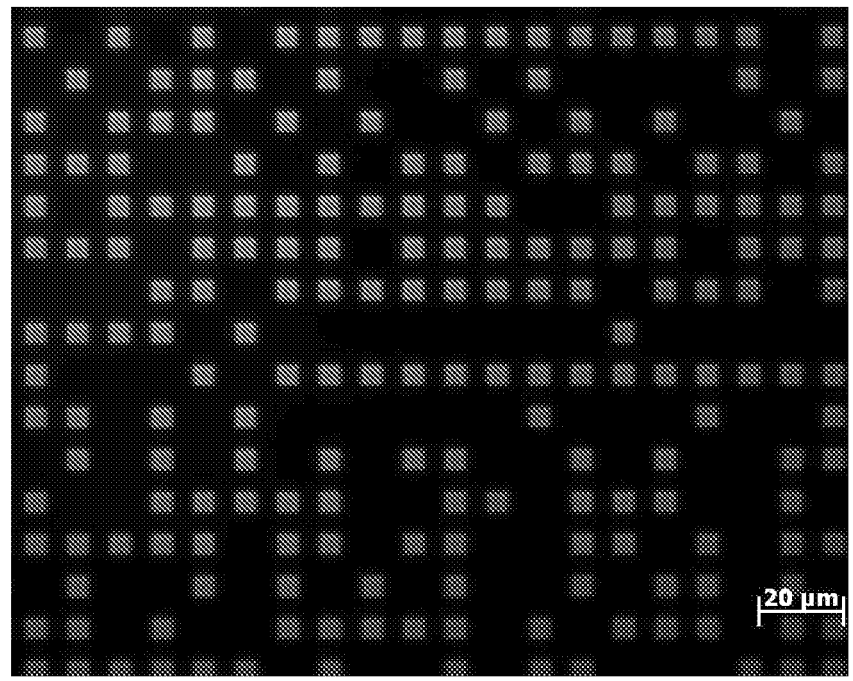
Figure 2:
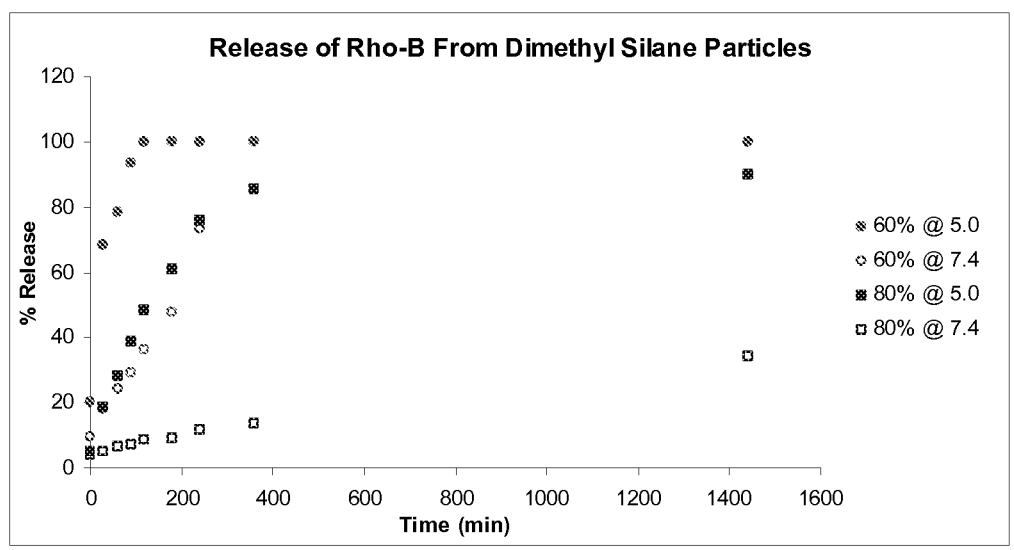
Figure 3:
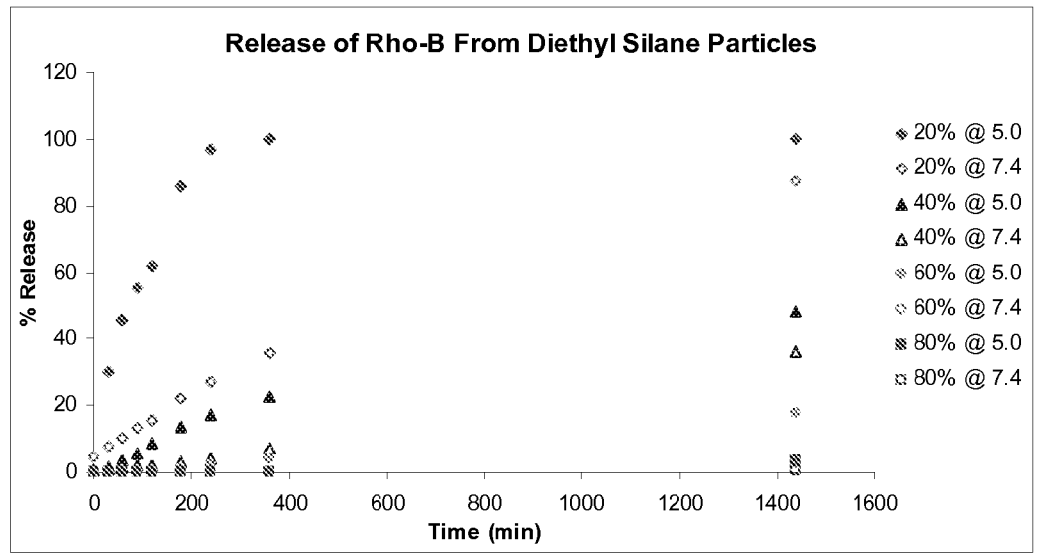
Figure 4:
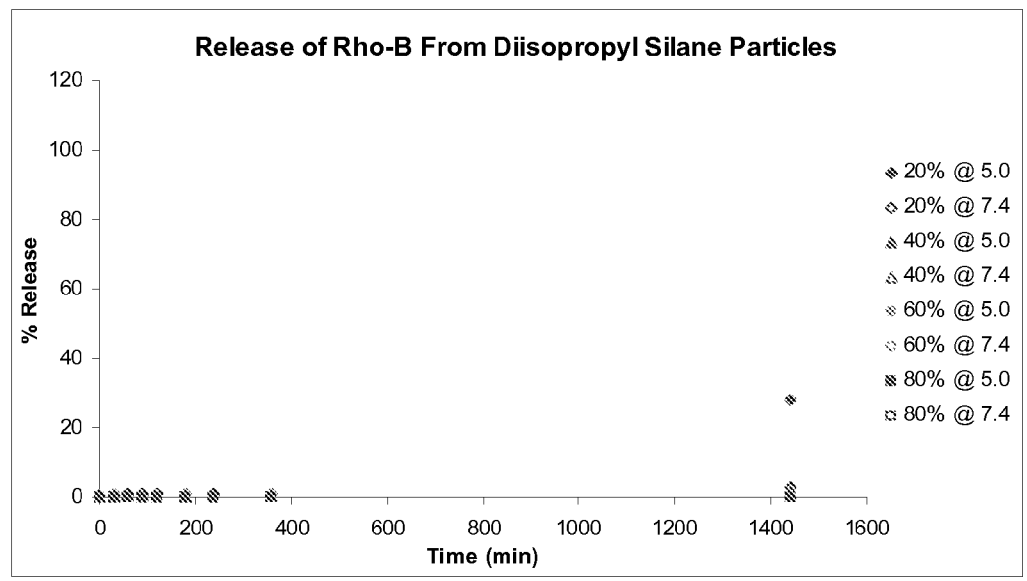
Figure 5:
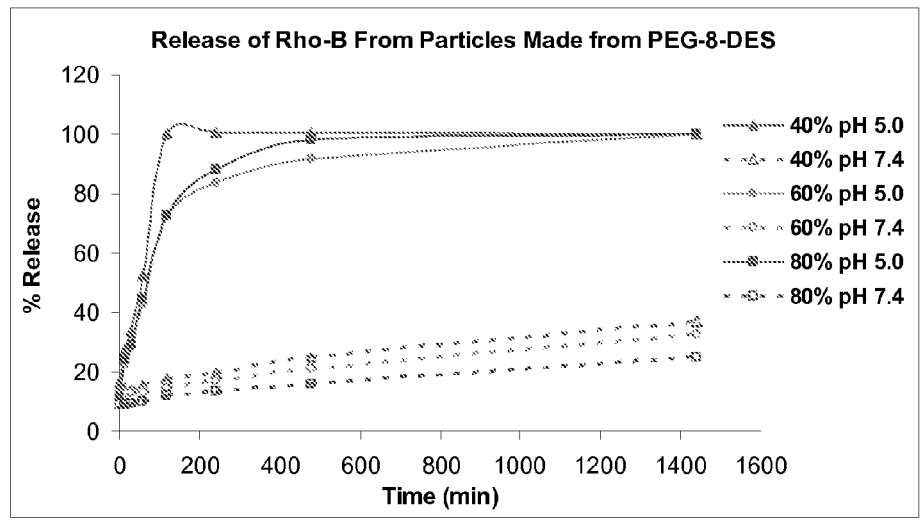
Figure 6:
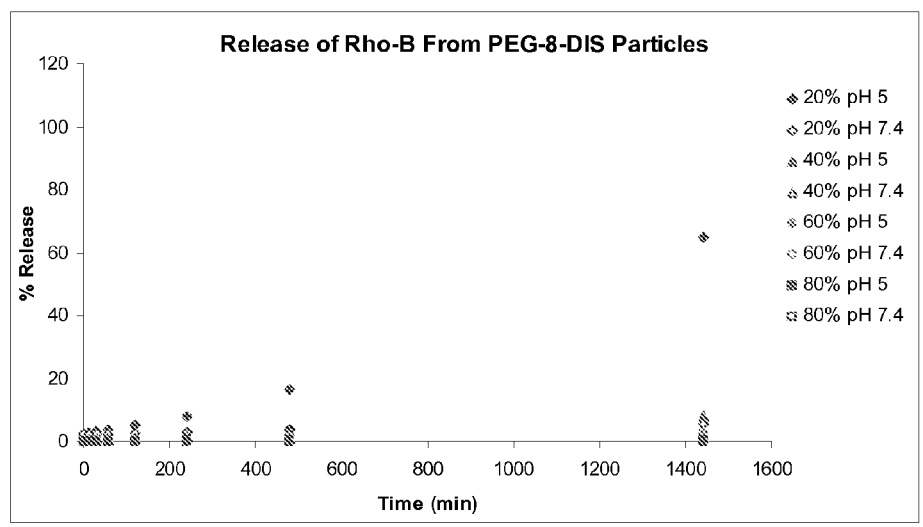
Figure 7:
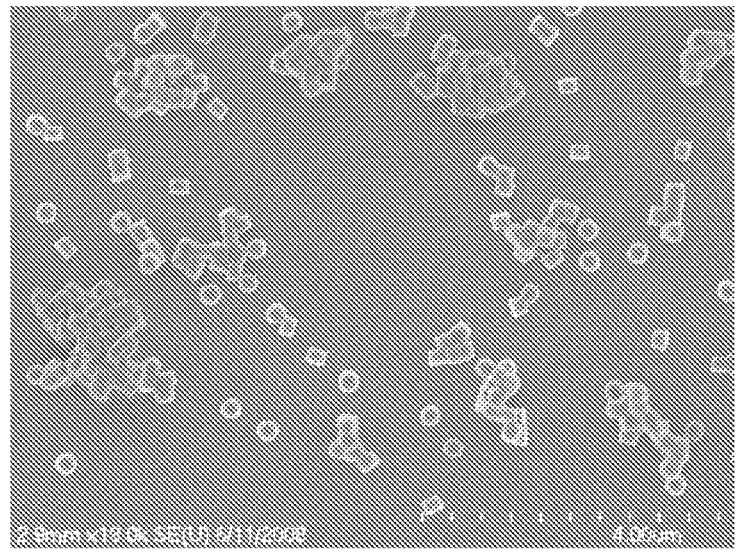
Figure 8:
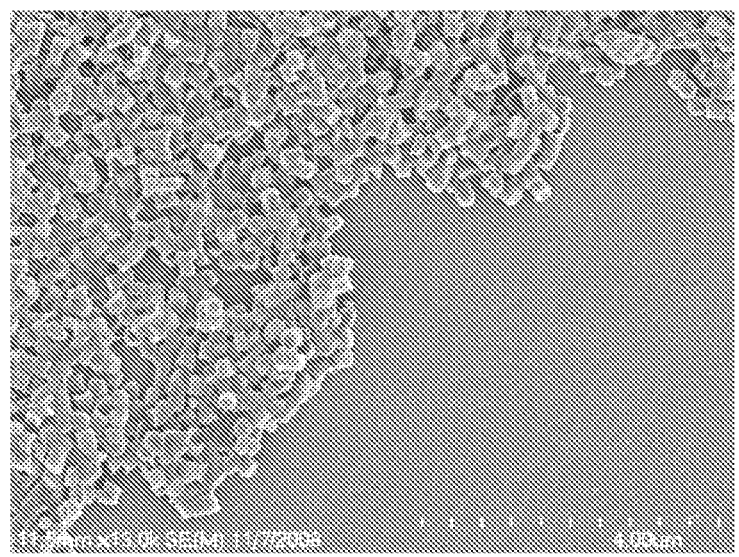
Figure 9:
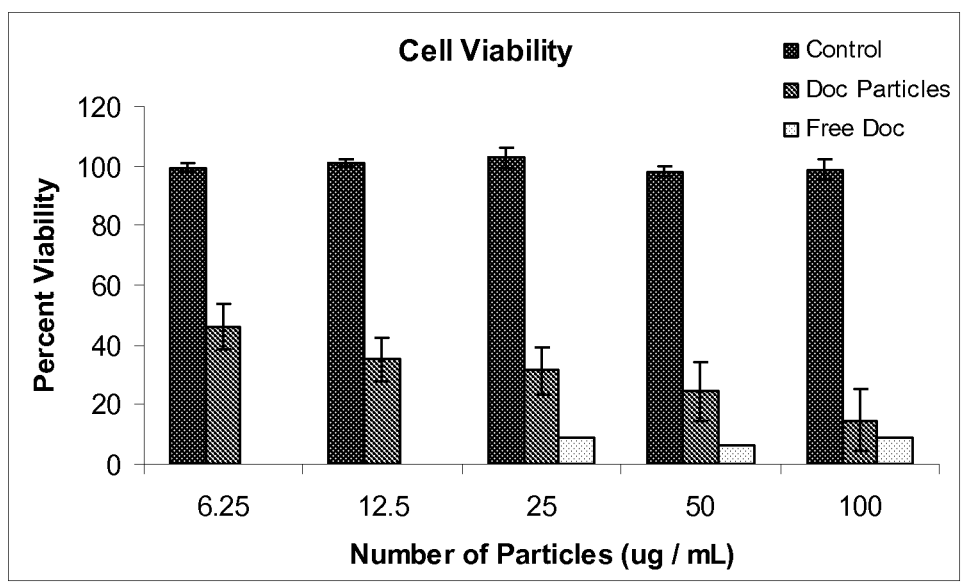

Having thus described the invention in general terms, reference will now be made to the accompanying drawings, wherein:

FIG. 1 is an optical microscope image of 5 μm particles made from a silyl ether crosslinker according to one embodiment of the invention having fluorescent rhodamine-B trapped within the polymer matrix;

FIG. 2 is a graph showing the release profile of rhodamine-B from particles made with 60% and 80% by weight of dimethyl silyl ether (DMS) crosslinker according to one embodiment of the invention at pH 5.0 and pH 7.4;

FIG. 3 is a graph showing the release profile of rhodamine-B from particles made with 20%, 40%, 60% and 80% by weight of diethyl silyl ether (DES) crosslinker according to one embodiment of the invention at pH 5.0 and pH 7.4;

FIG. 4 is a graph showing the release profile of rhodamine-B from particles made with 20%, 40%, 60% and 80% by weight of diisopropyl silyl ether (DIS) crosslinker according to one embodiment of the invention at pH 5.0 and pH 7.4;

FIG. 5 is a graph showing the release profile of rhodamine-B from particles made with 40%, 60% and 80% by weight of octaethylene glycol diethyl silyl ether (PEG-8-DES) crosslinker according to one embodiment of the invention at pH 5.0 and pH 7.4;

FIG. 6 is a graph showing the release profile of rhodamine-B from particles made with 20%, 40%, 60% and 80% by weight of octaethylene glycol diisopropyl silyl ether (PEG-8-DIS) crosslinker according to one embodiment of the invention at pH 5.0 and pH 7.4;

FIG. 7 is a scanning electron microscope image of 200 nm particles made from 98% by weight PEG-8-DES and 2% by weight DEAP, according to one embodiment of the invention;

FIG. 8 is a scanning electron microscope image of 200 nm particles made from 70% by weight PEG-8-DES, 24% by weight aminopropyl methacrylamide, 1% by weight DEAP, and 5% by weight docetaxel according to one embodiment of the invention; and FIG. 9 is a graph showing the results of a MTS assay of 200 nm particles dosed on HeLa (cervical cancer) cells, wherein the particles were formed using a PEG-8-DES compound according to one embodiment of the invention with or without docetaxel.

DETAILED DESCRIPTION OF THE INVENTION

The present inventions now will be described more fully hereinafter with reference to the accompanying drawings, in which one, but not all embodiments of the inventions are illustrated. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

I. Compounds

The compounds of the invention may be referred to herein as "degradable" compounds or "labile" compounds, but neither term should be viewed as expressly limiting the scope of the compounds. Rather, the terms "degradable" and "labile" merely are used to describe the nature of the compounds, in that the inventive compounds are stable under one or more defined conditions but, under one or more different specified conditions, the compounds will undergo a chemical transformation (e.g. cleavage). This transformation may be exemplified by the breaking of one or more bonds within the compound that causes the compound to become fragmented. The transformation also may be exemplified by the partial or complete solubilization of the compound under the specified conditions. Accordingly, the terms "degradable" and "labile" may mean the compounds are subject to being transformed by a variety of means, and a skilled person viewing the present description would be able to envision a variety of methods whereby the inventive compounds could be degraded according to the various uses described herein, and all of such methods are encompassed by the present invention. In various embodiments, the degradation may be dependant upon one or more of the following conditions: pH; radiation; ionic strength; oxidation; reduction; temperature; an alternating magnetic field; an alternating electric field; combinations thereof; or the like.

In one embodiment, the compounds of the invention may be described as "pH labile compounds" or "acid labile compounds". A pH labile compound is understood to mean a compound that may be chemically transformed (as described above) in relation to a change in pH. Accordingly, a pH labile compound may be stable at a pH below a certain value but degrade when pH is raised above the certain value. Likewise, a pH labile compound may be stable at a pH above a certain value but degrade when pH is lowered below the certain value. In a specific embodiment, an acid labile compound is stable above a pH of 7.9, 7.8, 7.7, 7.6, 7.5, 7.4, 7.3, 7.2, 7.1, or 7.0 but degrades below the specified value. In other embodiments, an acid labile compound can comprise a compound that is stable at a pH above about 7.5, above about 7, or above about 6.5 but degrades below this value.

In specific embodiments, a pH labile compound according to the invention may be described as being degradable at cellular pH conditions. For example, in some embodiments, the compounds of the invention (and compositions and particles incorporating the compounds) particularly may be designed to degrade under pH conditions typically found in cell endosomes.

In certain embodiments, the compounds of the invention comprise the following basic structure of Formula (1a),

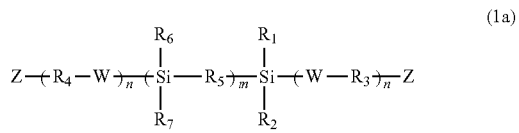

(1a)

wherein:

W is O, NH, N—CH$_3$, SH, S—CH$_3$, or C(O)O;

R$_1$, R$_2$, R$_6$, and R$_7$ are the same or different and are optionally substituted straight or branched chain C$_1$-C$_6$ alkyl, alkenyl, or alkynyl; optionally substituted C$_3$-C$_6$ cycloalkyl, cycloalkenyl, or cycloalkynyl; optionally substituted phenyl or benzyl; or optionally substituted polyether or polyester;

R$_3$ and R$_4$ are the same or different and are optionally substituted straight or branched chain C$_1$-C$_{12}$ alkyl, alkenyl, or alkynyl; or optionally substituted polyether or polyester;

R$_5$ is (W)$_p$—Y—(W)$_p$;

Y is optionally substituted straight or branched chain C$_1$-C$_{12}$ alkyl, alkenyl, or alkynyl; or optionally substituted polyether or polyester;

p is 0 or 1;

each Z is independently a polymerizable group;

m is an integer from 0 to 6; and n is an integer from 0 to 30.

The use of the phrase "optionally substituted" herein indicates that each C atom includes the appropriate number of H atoms to equal four bonds per carbon, or one or more H atoms may be replaced by a substituent. Preferred substituents are straight or branched chain $C_1$-$C_4$ alkyl, alkenyl, or alkynyl groups.

A polymerizable group, as used herein is understood to be any group that facilitates polymerization of the overall molecule to which it is attached, such as through reaction with another identical molecule (e.g., homopolymerization) or a different molecule (e.g., co-polymerization). In specific embodiments, a polymerizable group is a group that facilitates polymerization to form a homopolymer of repeating identical subunits. Thus, in certain embodiments, the compounds of the invention can be referred to as oligomers comprising polymerizable functional groups.

Non-limiting examples of polymerizable groups useful according to the present invention include groups comprising a terminal C=C bond and groups comprising a C=O bond. In particular embodiments, polymerizable groups in the compounds according to the invention comprise groups that are UV polymerizable (i.e., wherein polymerization proceeds upon application of ultraviolet light stimulus). Non-limiting examples of UV polymerizable groups useful according to the invention include acrylate and methacrylate groups (e.g., groups comprising a moiety from acrylic acid or methacrylic acid). Yet further examples of polymerizable groups useful according to the invention include maleimide, acrylamide, and methacrylamide groups. In some embodiments, the polymerizable group on the compound of Formula (1) is selected from the group consisting of an acrylate moiety, a methacrylate moiety, an epoxy moiety, an amino moiety, a carboxylic moiety, an anhydride moiety, a maleimide moiety, an isocyanate moiety, an olefinic moiety, a styrenic moiety, an acrylamide moiety, a methacrylamide moiety, and combinations thereof. It is understood that the foregoing list is only exemplary, and the invention fully encompasses any polymerizable group for use as the Z component.

In specific embodiments, $R_1$, $R_2$, $R_6$, and $R_7$ particularly may be methyl, ethyl, propyl, isopropyl, butyl, tert-butyl, or phenyl; $R_3$ and $R_4$ particularly may be methyl, ethyl, or straight or branched chain propyl, butyl, pentyl, hexyl, heptyl, octyl, nonyl, or decyl; Z particularly may be an acrylate moiety, a methacrylate moiety, or a maleimide moiety, m particularly may be 0 or 1, Y particularly may be methyl or ethyl, p particularly may be 0 or 1, and n particularly may be 1, 2, 3, 4, 5, 6, 7, 8, 9, or 10.

In certain other embodiments, the compounds of the invention comprise the following basic structure of Formula (1b),

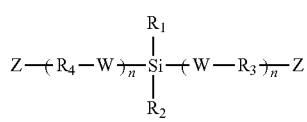
(1b)

wherein: W, $R_1$, $R_2$, $R_3$, $R_4$, Z, and n are as described above in relation to Formula (1a).

In particular embodiments, the compounds according to the invention particularly include compounds wherein W is O. According to such embodiments, the present invention encompasses compounds according to the Formula (2),

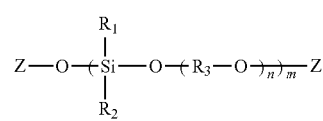
(2)

wherein $R_1$, $R_2$, $R_3$, Z, m, and n are as defined herein. In further embodiments, the present invention also encompasses compounds according to Formula (3),

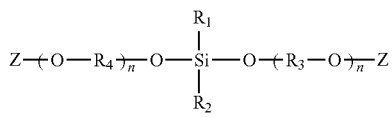
(3)

wherein $R_1$, $R_2$, $R_3$, $R_4$, Z, and n are as defined herein (each n being independent of the other). In still further embodiments, the present invention encompasses compounds according to Formula (4),

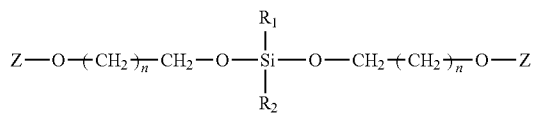
(4)

wherein $R_1$, $R_2$, Z, and n are as defined herein. In particular embodiments, n may be an integer from 0 to 10. In yet other embodiments, the present invention encompasses compounds according to Formula (5),

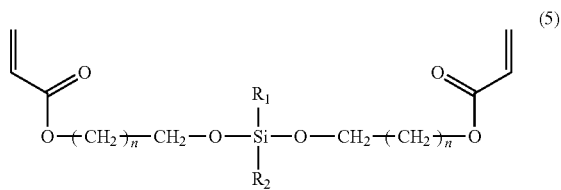
(5)

wherein $R_1$, $R_2$, and n are as defined herein. In still other embodiments, the present invention encompasses compounds according to the Formula (6),

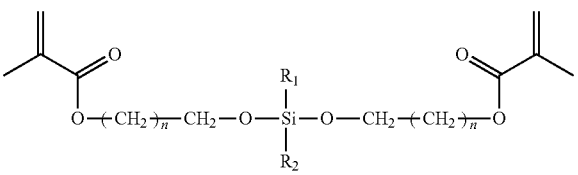
(6)

wherein $R_1$, $R_2$, and n are as defined herein.

Specific, non-limiting examples of compounds encompassed according to the invention are provided below in the structures of Formula (7) through Formula (14), wherein R is methyl, ethyl, or isopropyl.

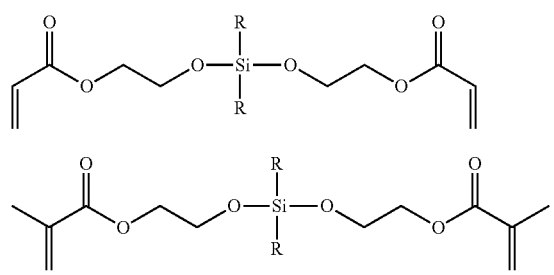

(7)

(8)

(9)

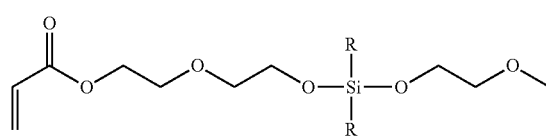

(10)

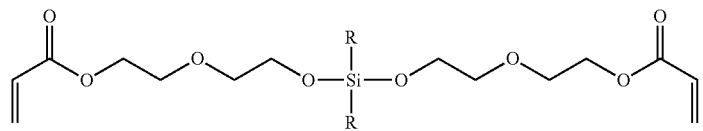

(11)

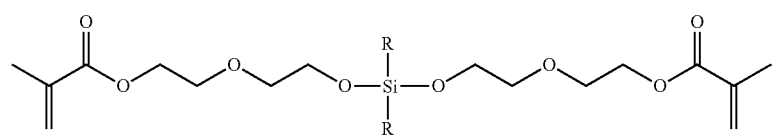

(12)

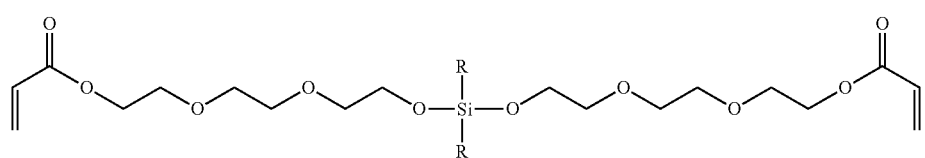

(13)

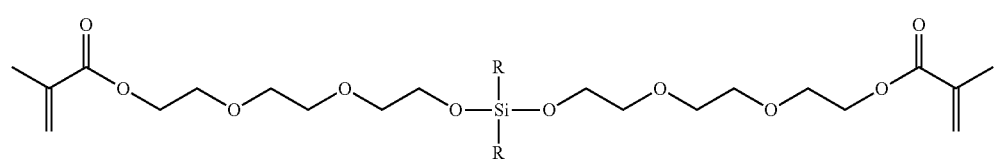

(14)

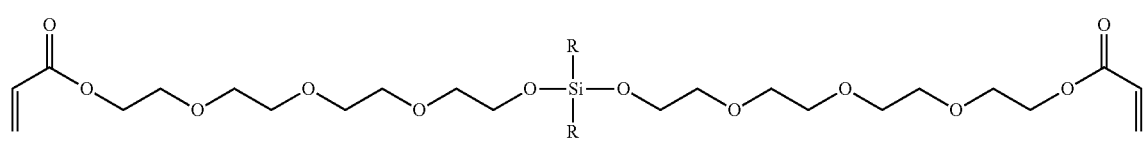

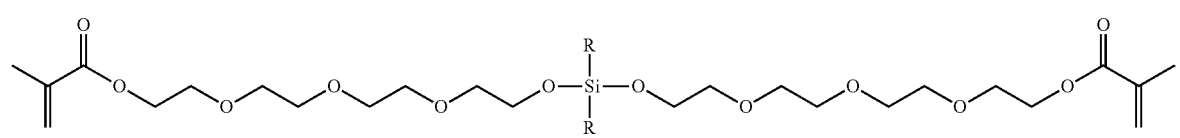

The present invention further comprises methods of preparing a degradable or labile compound as described herein. In particular, the compounds of the invention can be prepared according to a variety of methods wherein one or more compounds comprising one or more silicon atoms are reacted with one or more organic compounds, wherein the reaction forms a compound including one or more degradable or labile regions. In particular, the method of the invention can be a method useful for forming compounds including the basic structure —Si—O—C—, —Si—NH—C—, —Si—SH—C—, or —Si—C(O)O—C—, such structures being particularly useful for forming degradable compounds.

In certain embodiments, compounds of the invention can be prepared by reacting a functionalized silane compound with a functionalized organic compound. A silane compound for use according to the present invention can be a compound having the formula $SiH_4$, wherein one, two, or three H atoms are replaced with a functional group or leaving group, and one, two, or three H atoms are replaced with an organic group.

In certain embodiments, the functional group(s) on the silane compound are selected from halogen (particularly chloro or bromo) or acetate. Of course, other functional groups that react with groups on organic compounds, such as alcohol groups, acid groups, and amine groups, could also be used as the silane functional group(s) according to the invention. The organic group(s) on the silane compound can vary and can particularly be chosen to increase or decrease degradation of the finally prepared compound of the invention, as more fully described below. In certain embodiments, the organic group(s) are selected from straight or branched chain $C_1$-$C_6$ alkyl, alkenyl, or alkynyl, $C_3$-$C_6$ cycloalkyl, cycloalkenyl, or cycloalkynyl, phenyl groups, and benzyl groups. Of course, such organic groups could be optionally substituted as described above. Selection of organic groups on the silane compound can be particularly important for controlling degradation properties of the formed degradable compound of the invention. While not wishing to be bound by theory, it is believed that shorter chain length organic groups allow for more rapid compound degradation while longer chain length organic groups allow for more delayed compound degradation. Thus, the organic groups on the silane compound may be selected to provide a protecting effect and delay compound degradation. For example, it has been determined according to the invention that the rate of hydrolysis of methyl (Me), ethyl (Et), isopropyl (iPr), and t-butyl (tBu) alkoxy silanes is as follows: Si—OMe>Si—OEt>Si—OiPr>Si—OtBu. This protecting effect is further described below in relation to Reaction Schemes III and IV.

The functionalized organic compound that is reacted with the functionalized silane compound can be selected from a variety of compounds including a functional group that will react with the functionalized silane compound to form a compound including a degradable or labile region. Non-limiting examples of such compounds include alcohols, acids (e.g., carboxylic acids), esters (e.g., carboxylates), thiols, and amines. It is particularly advantageous to use di-functionalized compounds (e.g., diols, diacids, diesters, dithiols, and diamines). In specific embodiments, the functionalized organic compound may be selected from the group of ethylene glycol, propylene glycol, polymers and co-polymers of ethylene glycol (e.g., PEG) and propylene glycol, PEG diols, polypropylene oxide (PPO) diols, oligopolyesters, polyglycolic lactic acid (PGLA) compounds, adipic acid, terephthalic acid, and combinations thereof. Particular, non-limiting examples of diamines useful according to the invention include ethylenediamine or any compound with structure $H_2N(CH_2)_nNH_2$ where n=2-6. Additional examples include aryl-diamines, such as benzene-1,4-diamine A reaction scheme for preparing a degradable compound according to the present invention is provided below in Reaction Scheme I. This illustrates one embodiment of the invention wherein a symmetrical compound is formed using a difunctionalized, disubstituted silane compound and an acrylate compound.

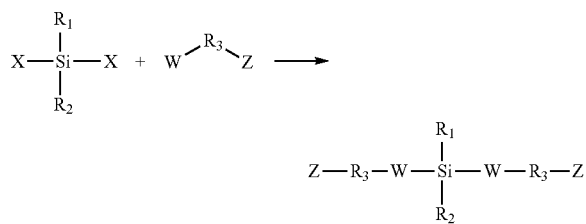

Reaction Scheme I

In Reaction Scheme I, $R_1$, $R_2$, $R_3$, W, and Z are as defined herein, and X is halo or acetate. From this reaction, it is evident that W, $R_3$, and Z can all be provided as a single compound for reaction with the silane compound. For example, in some embodiments, hydroxyethyl acrylate (HEA) or hydroxyethyl methacrylate (HEMA) may be reacted with the silane compound, the HEA or HEMA providing the polymerizable group, as well as the O atom for forming the degradable —Si—O—C— portion of the compound. For illustrative purposes, a specific reaction for forming a degradable compound according to the invention is provided below in Reaction Scheme II.

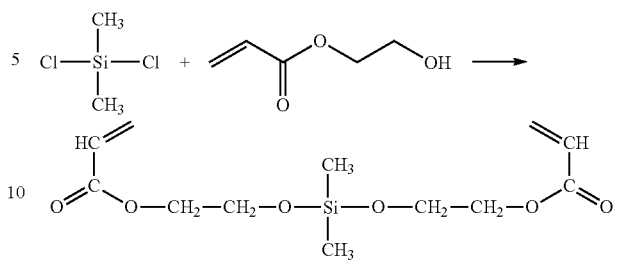

Reaction Scheme II

As seen in Reaction Scheme II, dichloro-diakyl silane is reacted with HEA to form the compound dialkyldi(acryloyoxy-1-ethoxy)silane.

Generally, in certain embodiments, the degradable compounds of the invention can be prepared by dissolving the silane compound and the organic compound in a suitable solvent (e.g., dichloromethane). To this mixture is added a base catalyst, such as triethylamine (TEA). Generally, the base catalyst can be any compound useful to deprotonate a hydroxyl group to make the group more reactive with the functionalized silane (e.g., a Si—Cl bond). In specific embodiments, the base catalyst may also be a compound that is further useful as an acid scavenger. For example, when the functional groups on the silane compound are halos (e.g., Cl or Br), the reaction produces a halo acid (e.g., HCl or HBr), and such acids could degrade the desired reaction product without the presence of the acid scavenger. For example, when TEA base is added to the reaction, it forms a stable, non-reactive salt with the HCl (or other acid). After addition, the base catalyst is stirred for a time suitable to allow for complete reaction. The solvent can then be removed, such as by rotary evaporation. The formed compound can be isolated, such as by column chromatography. Such methods are further described in the appended Examples.

In certain embodiments, compounds according to the invention can be prepared by reacting a water soluble polymer containing alcoholic groups with a functionalized silane to form a silane protected polyol. The silane can be as described above. In this embodiment, polymers containing alcoholic groups potentially can be rendered water insoluble using di- and tri-alkyl silane groups. By selecting the appropriate organic groups the polymer could be rendered insoluble and stable at pH 7, but at lower pH's the silane protecting groups will begin to hydrolyze. After a certain degree of hydrolysis of the silane groups, the polymer will become water-soluble again. Particles of this invention could be designed for stability under neutral pH conditions and then dissolve rapidly at the pH's found in tumors, endosomes, lysosomes, and other physiological matter exhibiting the correct pH conditions. An exemplary reaction is given below in Reaction Scheme III.

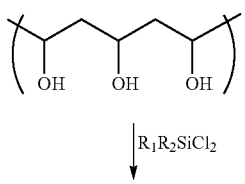

Reaction Scheme III

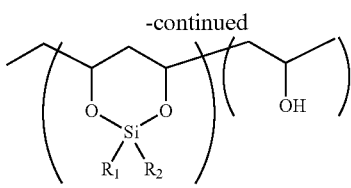

In specific embodiments, the polymers may be selected from the group of poly(vinylpyrrolidone)-co-poly(vinylalcohol), poly(HEMA), poly(HEA), co-polymers of HEMA/HEA and PVP or acrylamides, polysaccharides (e.g. dextran or arabinogalactan), combinations thereof, and the like.

Similar to a protected polyol, the alcohol group of the monomer can be protected prior to polymerization. Thus, it is possible to form polymerizable monomers for use in forming protecting polymers. An exemplary structure is provided below in the compound of Formula (15),

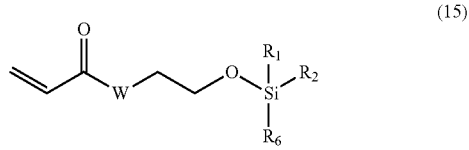

(15)

wherein $R_1$, $R_2$, $R_6$ and W are as described above. This potentially allows the introduction of other UV curable monomers into the polymer. Non-limiting examples or other moieties that may be included are crosslinkers, charged monomers, targeting ligands, hydrophilic monomers, non-degradable hydrophobic monomers, combinations thereof, and the like.

In further embodiments of the present invention, poly(carboxylic acid) polymers can be protected with a trialkylsilyl group to render the polymer insoluble. An exemplary scheme for preparing such silane protected polyacids is provided below in Reaction Scheme IV. As can be appreciated from earlier embodiments, the degree of protection and substituents of the silane group should tune the solubility and degradation of the polymer.

Reaction Scheme IV

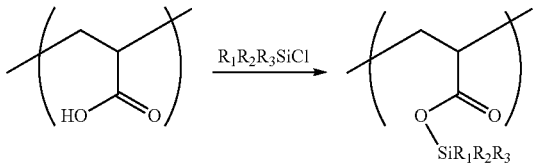

In specific embodiments, the polymers may be selected from: polyacrylic acid, poly(methacrylic acid), poly(propacrylic) acid, poly(ethacrylic acid),poly(acrylic acid-co-vinyl pyrrolidone), poly(acrylic acid-co-acrylamide), combinations thereof, and the like.

In light of the foregoing, the present invention encompasses polymers that are rendered insoluble in water by the introduction of the hydrophobic silane groups. When the silane groups are removed (such as under acidic conditions), it allows the polymer to become water soluble again, making any particle formed using the polymers able to dissolve/degrade rapidly. As in Reaction Scheme III, this would work with any polymer that has 1,3-diol functionality (given sufficient functionality to render the polymer water insoluble). As in Reaction Scheme IV, it would work with any polymer the contained a carboxylic acid in sufficient functionality to render water insoluble once protected with the silane.

Accordingly, in one embodiment, the invention provides protected compositions, which may comprise protected particles, and which are formed using water-soluble polymers. The compositions and/or particles are protected in that they will not solubilize under a first set of conditions but will solubilize under a second set of conditions. In some embodiments, the condition is pH. For example, the compositions and/or particles are protected in that they will not solubilize in aqueous conditions at a pH of greater than about 8, greater than about 7.5, greater than about 7.0, greater than about 6.5, or greater than about 6. In other embodiments, the compositions and/or particles are protected in that they will solubilize in aqueous conditions at a pH of less than about 7.5, less than about 7.0, less than about 6.5, or less than about 6.0.

As described below, the invention particularly encompasses particles formed using various materials as described herein. Thus, in certain embodiments, the invention comprises particles formed of a water-soluble polymer and that comprise a compound according to the invention that includes a silane group.

II. Delivery Compositions

The degradable or labile compounds of the invention particularly may be useful in the preparation of compositions for delivery of a desired drug, compound, or other biologically active material. The degradable nature of the compounds according to the invention allow for the formation of compositions that are stable under defined conditions (e.g., ambient conditions) but are degradable under different specified conditions (e.g., at body temperature—about 37° C., or under specific pH conditions). These compositions can include a component for delivery to the site of interest, wherein the composition will degrade and release the component for delivery.

The compositions of the invention may be formed of an organic material or an inorganic material and may be one uniform compound or component or a mixture of compounds or components. According to some embodiments, a material used in the composition may be a high molecular weight material, may comprise more than about 50% by weight liquid, may comprise less than about 50% by weight liquid, or may comprise less than about 10% by weight liquid. In particular embodiments, a material used in forming the present composition may include, without limitation, one or more of a polymer, a liquid polymer, a solution, a monomer, a plurality of monomers, a charged monomer, a water soluble monomer, a polymerization initiator, a polymerization catalyst, an inorganic precursor, an organic material, a natural product, a metal precursor, a pharmaceutical agent, a tag, a magnetic material, a paramagnetic material, a ligand, a cell penetrating peptide, a porogen, a surfactant, a plurality of immiscible liquids, a solvent, a charged species, combinations thereof, or the like. In some embodiment, the material to be molded in cavities of the mold include, but are not limited to, photovoltaic materials, optical materials, transparent materials, translucent materials, opaque materials, conductive materials, combinations thereof, and the like.

According to some embodiments, the inventive composition is hydrophilic such that the composition (and structures made therewith) avoids clearance by a biological organism, such as a human. In particular embodiments, compositions according to the invention generally may be characterized as comprising a matrix material and a cargo component.

II.a. Matrix Material

The matrix material particularly comprises a degradable or labile compound as described herein. In some embodiments, the degradable compound according to the invention may be used as the matrix material itself For example, the degradable compound could be formed using a high molecular weight PEG compound or other similar compound useful to form a matrix, particularly a matrix that may be formed into discrete particles, as further described below. In other embodiments, a degradable compound according to the invention may be a crosslinker compound that is combined with one or more further matrix-forming compounds to form a degradable matrix (the degradation being made possible by the presence of the inventive degradable compound in the form of a crosslinker compound). Likewise, the degradable compound of the invention could be a polymeric material that may be co-polymerized with another material to form the matrix of the composition. In certain embodiments, In light of the wide variety of possible matrices that may be prepared using a degradable compound as described herein, the matrix material may comprise varying amounts of the degradable compound. Generally, the degradable compound may comprise about 0.1% to about 99.9% by weight of the matrix material. For example, when the degradable compound is used as a cross-linker, the degradable material may comprise about 0.1% to about 50% by weight of the matrix material, about 0.1% to about 40%, about 0.1% to about 30%, about 0.1% to about 20%, about 0.1% to about 15%, about 0.1% to about 10%, about 1% to about 10%, or about 2% to about 10% by weight of the matrix material. When the degradable compound is used to form the matrix material generally, the degradable compound may comprise about 50% to about 99.9% by weight of the matrix material, about 60% to about 99.9%, about 70% to about 99.9%, about 80% to about 99.9%, or about 90% to about 99.9% by weight of the matrix material. When the degradable compound is used as a co-polymer to form the matrix material, the degradable material may comprise about 10% to about 90% by weight of the matrix material, about 20% to about 90%, about 30% to about 90%, about 40% to about 90%, about 50% to about 90%, about 60% to about 90%, or about 70% to about 90% by weight of the matrix material.

Non-limiting examples of monomeric materials that may be used to form a matrix material for use in the inventive compositions include amines, amine salts, diamines, imidines, guanadines, imines, hydroxylamines, hydrazines, imidazoles, morpholines, pyrimidines, pyrenes, sulfates, sulfonates, carboxylates, phosphates, butadienes, styrenes, propene, acrylates, methacrylates, vinyl ketones, vinyl esters, vinyl acetates, vinyl chlorides, vinyl fluorides, vinyl ethers, acrylonitrile, methacrylnitrile, acrylamide, methacrylamide allyl acetates, fumarates, maleates, ethylenes, propylenes, tetrafluoroethylene, ethers, isobutylene, fumaronitrile, vinyl alcohols, acrylic acids, amides, carbohydrates, esters, urethanes, siloxanes, formaldehyde, phenol, urea, melamine, isoprene, isocyanates, epoxides, bisphenol A, alcohols, chlorosilanes, dihalides, dienes, alkyl olefins, ketones, aldehydes, vinylidene chloride, anhydrides, saccharide, acetylenes, naphthalenes, pyridines, lactams, lactones, acetals, thiiranes, episulfide, peptides, derivatives thereof, and combinations thereof. Such monomeric units could be combined with degradable compounds according to the invention and be co-polymerized to form a degradable co-polymer matrix material. Likewise, the degradable compounds according to the invention could be used as crosslinkers to facilitate crosslinking of one or more of the monomers illustrated above to form a matrix having degradable crosslinks. In some embodiments, exemplary monomeric materials may include hydroxyethyl methacrylate, polyethyleneglycol monoacrylate, or any other mono-functional acrylate, methacrylate, acrylamide, or methacrylamide monomer that will form a water-soluble linear polymer. Non-limiting, specific examples of monomers that could be used with the degradable compounds of the invention to form a matrix material are amino ethyl methacrylate (AEM), dimethylamino ethyl acrylate (DMAEA) and aminopropyl methacrylamide (APMAM).

In other embodiments, the matrix of the composition may be described in terms of specific polymers used to form the matrix. Non-limiting examples of polymers that may be used to form the matrix include polyamides, proteins, polyesters, polystyrene, polyethers, polyketones, polysulfones, polyurethanes, polysiloxanes, polysilanes, cellulose, amylose, polyacetals, polyethylene, glycols, poly(acrylate)s, poly(methacrylate)s, poly(vinyl alcohol), poly(vinylidene chloride), poly(vinyl acetate), poly(ethylene glycol), polystyrene, polyisoprene, polyisobutylenes, poly(vinyl chloride), polyvinyl pyrrolidone, poly(propylene), poly(lactic acid), polyisocyanates, polycarbonates, alkyds, phenolics, epoxy resins, polysulfides, polyimides, liquid crystal polymers, heterocyclic polymers, polypeptides, conducting polymers including polyacetylene, polyquinoline, polyaniline, polypyrrole, polythiophene, and poly(p-phenylene), dendimers, fluoropolymers, derivatives thereof, and combinations thereof. Such polymers could be combined with degradable compounds according to the invention to form a degradable matrix material. Likewise, such polymers could be formed using the degradable compounds of the invention as crosslinkers so that that disclosed polymers include degradable crosslinks.

Matrix materials may be chosen to meet specific needs or use conditions. For example, different monomers and polymers are known to be hydrophilic or lipophilic. Thus, it is possible in various embodiments of the invention to customize the hydrophilic or lipophilic nature of the matrix material by choosing the type or ratio of monomer and polymers used to form the matrix. For example, when desirable to prepare compositions that may cross a lipophilic cell membrane, the matrix material may be particularly chosen to have a desired lipophilic nature. Likewise, for use in conditions where hydrophilic properties are desired, the matrix material may be chosen to have a desired hydrophilic nature.

In addition to the use of the degradable compounds of the invention, the matrix material used to form the inventive compositions may also include one or more biodegradable polymers. The use of biodegradable polymers can facilitate delivery of the cargo component. More desirably, though, the use of biodegradable polymers facilitates the removal of the matrix material from the delivery site after delivery of the cargo component via degradation of the degradable compound of the invention. In some embodiments, the biodegradable polymer includes, without limitation, one or more of a polyester, a polyanhydride, a polyamide, a phosphorous-based polymer, a poly(cyanoacrylate), a polyurethane, a polyorthoester, a polydihydropyran, a polyacetal, combinations thereof, or the like. In some embodiments, specific non-limiting examples of a polyester include one or more of polylactic acid, polyglycolic acid, poly(hydroxybutyrate), poly($\epsilon$-caprolactone), poly($\beta$-malic acid), poly(dioxanones), combinations thereof, or the like. Specific, non-limiting examples of a polyanhydride include one or more of poly (sebacic acid), poly(adipic acid), poly(terpthalic acid), combinations thereof, or the like. Specific, non-limiting examples of a polyamide include one or more of poly(imino carbonates), polyaminoacids, combinations thereof, or the like. Specific, non-limiting examples of a phosphorous-based polymer include one or more of a polyphosphate, a polyphosphonate, a polyphosphazene, combinations thereof, or the like.

In still further embodiments, the material used to prepare the matrix of the inventive composition may include a non-wetting agent. Moreover, the material may be described in terms of a specific phase, such as being a liquid material in a single phase or being a liquid material including a plurality of phases. In some embodiments, the liquid material may include, without limitation, one or more of multiple liquids, multiple immiscible liquids, surfactants, dispersions, emulsions, micro-emulsions, micelles, particulates, colloids, porogens, active ingredients, combinations thereof, or the like.

II.b. Cargo Component

In certain embodiments, a composition according to the present invention may comprise a cargo component, which may include any material that may be desirable for delivery to a specific location, particularly in a living organism. In some embodiments the cargo component may include biologically active cargo, an elemental material, a molecule, a chemical substance, an agent, a therapeutic agent, a diagnostic agent, a pharmaceutical agent, a drug, a medication, genetic material, a nucleotide sequence, an amino-acid sequence, a ligand, an oligopeptide, a protein, a vaccine, a biologic, DNA, RNA, a cancer treatment, a viral treatment, a bacterial treatment, a fungal treatment, an auto-immune treatment, a psychotherapeutic agent, an imaging agent, a contrast agent, an antisense agent, radiotracers and/or radiopharmaceuticals combinations thereof, and the like. In some embodiments the oligonucleotide includes, but is not limited to an RNA, siRNA, dsRNA, ssRNA, miRNA, rRNA, tRNA, snRNA, shRNA, DNA, ssDNA, dsDNA, plasmid DNA, or a vaccine. In particular embodiments, the cargo component may be selected from the group consisting of biologically active materials, elemental materials, therapeutic agents, diagnostic agents, drugs, genetic materials, nucleotide sequences, amino-acid sequences, ligands, oligopeptides, proteins, vaccines, biologics, DNA, RNA, imaging agents, contrast agents, antisense agents, radiotracers, radiopharmaceuticals, and combinations thereof. In specific embodiments, a drug may be selected from the group consisting of anti-cancer agents, antiviral agents, anti-bacterial agents, anti-fungal agents, anti-autoimmunity agents, and psychotherapeutic agents.

The cargo component and the matrix material may be combined via a variety of means. Such combination may be described as the cargo component being associated with the matrix material. In embodiments wherein the matrix material, the degradable compound, or a combination thereof is in the form of a particle, the cargo component may be described as being associated with the particle. For example, the cargo component may be at least partially encapsulated by the matrix material, the cargo component may be covalently bonded to one or more functional groups present on the matrix material, or the cargo component may be physically blended with the matrix material.

As more fully described below, the compositions of the invention may be used to form particular structures, such as discrete particles. In some embodiments of the invention, such structures may include a functional location such that the structure may be used as an analytical material. Accordingly, such structures may include a functional molecular imprint, which may include functional monomers arranged as a negative image of a functional template. The functional template, for example, can be but is not limited to, chemically functional and size and shape equivalents of an enzyme, a protein, an antibiotic, an antigen, a nucleotide sequence, an amino acid, a drug, a biologic, nucleic acid, combinations thereof, or the like. In other embodiments, the structure itself, for example, can be, but is not limited to, an artificial functional molecule. In one embodiment, the artificial functional molecule is a functionalized particle that has been molded from a molecular imprint. As such, a molecular imprint is generated in accordance with methods and materials of the presently disclosed subject matter and then a particle is formed from the molecular imprint, in accordance with further methods and materials of the presently disclosed subject matter. Such an artificial functional molecule includes substantially similar steric and chemical properties of a molecular imprint template. In one embodiment, the functional monomers of the functionalized particle are arranged substantially as a negative image of functional groups of the molecular imprint.

In some embodiments, additional components may be included with the composition to functionalize a structure (e.g., a particle) that may be formed using the composition. According to these embodiments the additional components can be encased within the isolated structures, partially encased within the isolated structures, on the exterior surface of the isolated structures, combinations thereof, or the like. Additional components can include, but are not limited to, drugs, biologics, more than one drug, more than one biologic, combinations thereof, and the like.

The cargo component of the inventive composition particularly may comprise one or more drugs. Non-limiting examples of drugs that may comprise the cargo component include the following: psychotherapeutic agents, such as anti-depressants (e.g., sertraline, venlafaxine, paroxetine, bupropion, citalopram, fluoxetine, mirtazapine, escitalopram, and the like), anti-schizophrenics (e.g., olanzapine, risperidone, quetiapine, aripiprazole, ziprasidone, and the like), and agents for treating attention deficit disorder (ADD) or attention deficit hyperactivity disorder (ADHD) (e.g., methylphenidate, atomoxetine, amphetamine, dextroamphetamine, and the like); anti-cholesterol drugs (e.g., atorvastatin, simvastatin, pravastatin, ezetimibe, rosuvastatin, fenofibrate fluvastatin, and the like); cardiovascular drugs (e.g., amlodipine, valsartan, losartan, hydrochlorothiazide, metoprolol, candesartan, ramipril, irbesartan, amlodipine, benazepril, nifedipine, carvedilol, enalapril, telemisartan, quinapril, doxazosin mesylate, felodipine, lisinopril, and the like); blood modifiers (e.g., epoetin alfa, darbepoetin alfa, epoetin beta, clopidogrel, pegfilgrastim, filgrastim, enoxaparin, Factor VIIA, antihemophilic factor, immune globulin, and the like); anti-infective agents, such as anti-bacterials (e.g., azithromycin, amoxicillin, clavulanic acid, levofloxacin, clarithromycin, ceftriaxone, ciprofloxacin, piperacillin, tazobactam sodium, imipenem, cilastatin, linezolid, meropenem, cefuroxime, moxifloxacin, and the like), anti-virals (e.g., lamivudine, zidovudine, valacyclovir, peginterferon, lopinavir, ritonavir, tenofovir, efavirenz, abacavir, lamivudine, zidovudine, atazanavir, and the like), and anti-fungals (e.g., terbinafine, fluconazole, itraconazole, caspofungin acetate, and the like); drugs for treating gastrointestinal disorders (e.g., esomeprazole, lansoprazole, omeprazole, pantoprazole, rabeprazole, ranitidine, ondansetron, and the like); respiratory drugs (e.g., fluticasone, salmeterol, montelukast, budesonide, formoterol, fexofenadine, cetirizine, desloratadine, mometasone furoate, tiotropium, albuterol, ipratropium, palivizumab, and the like); antiarthritic drugs (e.g., celecoxib, infliximab, etanercept, rofecoxib, valdecoxib, adalimumab, meloxicam, diclofenac, fentanyl, and the like); anticancer agents (e.g., nitrogen mustard, cisplatin, doxorubicin, docetaxel, anastrozole, trastuzumab, capecitabine, letrozole, leuprolide, bicalutamide, goserelin, rituximab, oxaliplatin, bevacizumab, irinotecan, paclitaxel, carboplatin, imatinib, gemcitabine, temozolomide, gefitinib, and the like); diabetes drugs (e.g., rosiglitazone, pioglitazone, insulin, glimepiride, voglibose, and the like); anticonvulsants (e.g., gabapentin, topiramate, oxcarbazepine, carbamazepine, lamotrigine, divalproex, levetiracetam, and the like); bone metabolism regulators (e.g., alendronate, raloxifene, risedronate, zoledronic, and the like); multiple sclerosis drugs (e.g., interferon, glatiramer, copolymer-1, and the like); hormones (e.g., somatropin, norelgestromin, norethindrone, desogestrel, progestin, estrogen, octreotide, levothyroxine, testosterone, human growth hormone, and the like); urinary tract agents (e.g., tamsulosin, finasteride, tolterodine, and the like); immunosuppressants (e.g., mycophenolate mofetil, cyclosporine, tacrolimus, and the like); ophthalmic products (e.g., latanoprost, dorzolamide, botulinum, verteporfin, and the like); vaccines (e.g., pneumococcal, hepatitis, influenza, diphtheria, and the like); sedatives (e.g., zolpidem, zaleplon, eszopiclone, and the like); Alzheimer disease therapies (e.g., donepexil, rivastigmine, tacrine, and the like); sexual dysfunction therapies (e.g., ildenafil, tadalafil, alprostadil, levothyroxine, and the like); anesthetics (e.g., sevoflurane, propofol, mepivacaine, bupivacaine, ropivacaine, lidocaine, nesacaine, etidocaine, and the like); migraine drugs (e.g., sumatriptan, almotriptan, rizatriptan, naratriptan, and the like); infertility agents (e.g., follitropin, choriogonadotropin, menotropin, follicle stimulating hormone (FSH), and the like); weight control products (e.g., orlistat, dexfenfluramine, sibutramine, and the like); and combinations of the above listed drugs. According to other embodiments, the cargo component may comprise one or more other drugs found in Physician's Desk Reference, Thomson Healthcare, 59th Bk&Cr edition (2004), which is incorporated herein by reference in its entirety.

In still further embodiments, the cargo component may comprise one or more of the following: targeting ligands, such as cell-targeting peptides, cell-penetrating peptides, integrin receptor peptide (GRGDSP), melanocyte stimulating hormone, vasoactive intestinal peptide, anti-Her2 mouse antibodies and antibody fragments, and the like; vitamins; viruses; polysaccharides; cyclodextrins; liposomes; proteins; oligonucleotides; aptamers; optical nanoparticles, such as CdSe for optical applications; borate nanoparticles to aid in boron neutron capture therapy (BNCT) targets; combinations thereof; and the like.

The presence of the cargo component makes the present invention particularly useful for providing pharmaceutical formulations. Such formulations may comprise a pharmaceutically acceptable carrier, a degradable compound according to the invention, and one or more pharmaceutical materials. The term "pharmaceutical material" is intended to be non-limiting in scope and, in these embodiments, should be understood as encompassing any active material that may be delivered in a pharmaceutical formulation. Such active material may be any cargo material as described herein that would be recognized as being useful to provide a therapeutic effect (e.g., preventing, curing, ameliorating, or otherwise affecting a medical ore veterinary condition in a patient).

II.c. Discrete Particle Formation

In some embodiments, the compositions of the invention may be provided in the form of discrete particles, particularly discrete micro- and/or nanoparticles. Thus, the present invention is further directed to such discrete particles and methods of preparing such discrete particles, particularly discrete micro- and/or nanoparticles.

In some embodiments, the process for making the micro- and/or nanoparticles may include the use of a mold, which may particularly include a plurality of cavities. In some embodiments, the mold cavities may have a substantially predetermined size and shape.

Materials that can be useful with and/or as the mold materials used in the present invention include, in some embodiments, substantially solvent resistant, low surface energy polymeric materials. In other embodiments, the mold can be or include a solvent resistant elastomer-based material, such as but not limited to a fluoropolymer, a fluorinated elastomer-based material, a fluoropolyether, perfluoropolyether, combinations thereof, or the like. In some embodiments, the mold may be particularly designed to have a specific surface energy, preferably below a defined value. In specific embodiments, the mold can have a surface energy below about 25 mN/m, below about 20 mN/m, below about 18 mN/m, below about 15 mN/m, below about 12 mN/m, or below about 10 mN/m.

Representative substantially solvent resistant elastomer-based materials useful according to the invention include, but are not limited to, fluorinated elastomer-based materials. As used herein, the term "substantially solvent resistant" refers to a material, such as an elastomeric material that neither swells nor dissolves beyond a nominal amount in common hydrocarbon-based organic solvents or acidic or basic aqueous solutions. Representative fluorinated elastomer-based materials include, but are not limited to, fluoropolyether and perfluoropolyether (collectively PFPE) based materials.

The mold materials of the present invention further include photocurable and/or thermal curable components such that the PFPE materials can be cured from a liquid to a solid upon application of a treatment such as actinic radiation or thermal energy. PFPE materials and modified PFPE materials that are applicable to making the molds of the present invention are described herein and it will be appreciated that the materials described herein can be combined in numerous ways to form different mold materials for use in the present invention.

According to some embodiments, hardening or curing of a composition or other material, solution, dispersion, or the like of the present invention includes hardening. For example, hardening can be via chemical reaction, such as polymerization, phase change, melting/cooling transition, evaporation, moisture cure, combinations thereof, and the like.

In some embodiments of the present invention the mold and/or substrate materials are preferably one or more of the following: flexible, non-toxic, substantially UV transparent, highly gas permeable, highly fluorinated, have a high free volume, tough, have a low surface energy, are highly permeable to oxygen, are highly permeable to carbon dioxide, are highly permeable to nitrogen, or are substantially resistant to swelling, combinations thereof, and the like. The properties of these materials can be tuned over a wide range through the judicious choice of additives, fillers, reactive co-monomers, and functionalization agents.

In other embodiments, the mold or substrate used in the invention can include a material selected from, for example, a fluoropolymer, a perfluoropolyether, a fluoroolefin, an acrylate, a silicone such as for example polydimethylsiloxane (PDMS)or fluorinated PDMS, a styrenic, a fluorinated thermoplastic elastomer (TPE), a triazine fluoropolymer, a perfluorocyclobutyl, a fluorinated epoxy, a fluorinated monomer or fluorinated oligomer that can be polymerized or crosslinked, a combination thereof, or the like.

Further embodiments of molds of the present invention are disclosed in the following references, which are incorporated herein by reference in their entirety: PCT Publication WO 2007/021762, filed Aug. 9, 2006; PCT Publication WO 2005/084191, filed Feb. 14, 2005; and U.S. Patent Application Publication No. 2007/0275193, filed Aug. 11, 2006.

According to certain embodiments of the invention, particles and/or patterned films may be formed in cavities of the molds described above. For example, a substantially liquid composition may be applied to the mold to form particles and/or a patterned film. In some embodiments, substantially liquid composition includes a liquid precursor.

Particles and patterned films prepared according to the present invention particularly may be molded in low surface energy molds, methods, and materials described in PCT Publication WO 2007/030698, filed Sep. 7, 2006 and PCT Publication WO 2007/094829, filed Nov. 7, 2006, both of which are incorporated herein by reference in their entirety including all references cited therein.

A particle prepared according to the invention may have a size and shape that substantially mimics the size and shape of the cavity of the mold in which the particle was formed. In some embodiments, a particle has a substantially predetermined size and shape. Moreover, the manufacturing process may produce particles with inherent variations in shape. In some embodiments, the shape of the particles may vary from the shape of the mold, and the shape of the particles also may vary from the shape of other particles in the plurality of particles. In certain embodiments, the variations of the shape of the particles may be nanoscale variations. In other embodiments, the particles may have identical or substantially identical shapes.

Particles prepared using the compositions of the invention can comprise a wide variety of uses. Non-limiting examples of such uses include: drug delivery vectors, gene delivery vectors, disease detecting devices, disease locating devices, cosmetics, catalysts, sensors, detoxifying agents, abrasives, taggants, pharmaceutical agents, and biomarkers.

As previously pointed out, particles prepared using the compositions of the invention particularly can be of a size so as to be characterized as microparticles or nanoparticles. Since particles according to the invention may be formed to have a shape corresponding to a mold (e.g., the particle has a shape reflecting the shape of the mold within which the particle was formed), the mold used to prepare the particle may have a desired shape and/or a desired size. In particular embodiments, particles according to the present invention have and average dimension of less than about 500 µm, less than about 400 µm, less than about 300 µm, less than about 200 µm, or less than about 100 µm. Such dimension may be a minimum dimension, an intermediate dimension, or a maximum dimension. Moreover, the dimension may be a length, width, or diameter of the particle. Particularly, the dimension may be the largest dimension of the particle.

In some embodiments, the particle is a nano-scale particle. As used herein, a nanoparticle is meant to describe a particle having a maximum dimension (as described above) that is less than 50 µm. The dimension particularly can be measured across the largest portion of the particle that corresponds to the parameter being measured. In other embodiments, the dimension of the nanoparticle is less than 25 µm, less than 10 µm, less than about 5 µm, less than about 1 µm, less than about 900 nm, less than about 800 nm, less than about 700 nm, less than about 600 nm, less than about 500 nm, less than about 400 nm, less than about 300 nm, less than about 200 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm. In still other embodiments, the dimension of the nanoparticle is about 1 nm to about 1,000 nm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, about 1 nm to about 100 nm, about 1 nm to about 50 nm, about 10 nm to about 500 nm, about 10 nm to about 400 nm, about 10 nm to about 300 nm, about 10 nm to about 200 nm, about 10 nm to about 100 nm, about 20 nm to about 200 nm, about 20 nm to about 100 nm, about 50 nm to about 500 nm, about 50 nm to about 250 nm, about 50 nm to about 200 nm, or about 100 nm to about 500 nm. The dimension of the particle can be a predetermined dimension, a cross-sectional diameter, a circumferential dimension, or the like.

According to further embodiments, the particles of the invention may include patterned features that are of a particular dimension. In certain embodiments, the patterned features are about 2 nm in a dimension.

As described above, particles according to the invention can include means for attaching thereto a cargo component, such as a drug, and such particles particularly may include a degradable component as described herein. For example, in certain embodiments, the invention provides chlorosilyl-activated PRINT particles, which particularly may be used for the covalent surface attachment of various cargo components, such as hydroxy-containing drug and PEG moieties. Such formed particles beneficially include pH-sensitive silane bonds.

In one embodiment, activated PRINT particles can be formed to have functionalized surfaces, meaning the particles are formed to have one or more functional groups on an exposed surface of the particles that are available for bonding with a degradable compound according to the present invention. Non-limiting examples of functional groups that may be useful according to the invention are any groups terminating with one or more of the following: O (e.g., hydroxyl), NH, N—CH$_3$, SH, S—CH$_3$, or C(O)O.

PRINT particles with hydroxy-functionalized surfaces can be prepared from a number of acrylate-based monomers such as 2-hydroxyethylacrylate or PEG-acrylates. These surface hydroxyl groups can be activated using silane compounds as described herein, such as dialkyldichlorosilanes. Such activation results in the formation of monochlorosilyl groups on the particle surface. This is illustrated below in Reaction Scheme V, wherein $R_1$ and $R_2$ are as described herein.

Reaction Scheme V

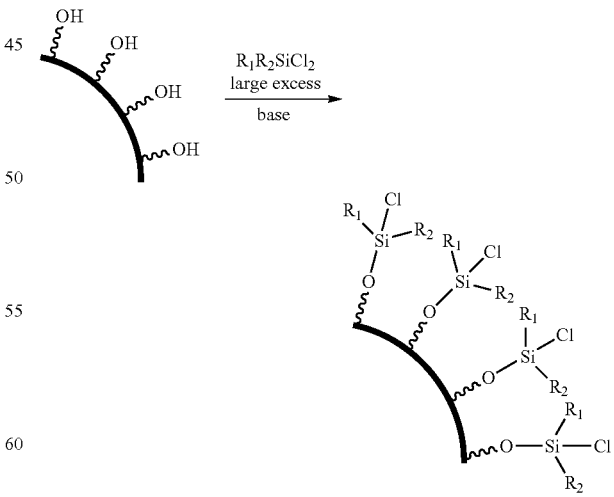

Thus, in certain embodiments, the present invention provides surface-activated microparticles or nanoparticles. By surface-activated is meant that the particles include one or more functionalized labile linkers including one or more functional group that can react with a group on a desired component (e.g., a drug or a group on a spacer molecule that in turn binds with or is bound to the desired species). For example, the functional group on the functionalized labile linker can be a halo group, such as chlorine.

In one embodiment, a surface-activated particle according to the invention may be described by the structure of Formula (16)

(16)

wherein $R_1$ and $R_2$ are as described herein, X is a reactive moiety, and "particle" indicates a linkage to a particle, as described herein. For example, the silane group may be O-linked to the particle. The reactive moiety particularly may be a halo group.

The surface-activated particles (e.g., chlorosilyl-activated particles) can be reacted with any component (e.g., drugs or other small molecule therapeutics, PEG chains, folic acid, etc.) having a suitable functional group thereon to form pH-sensitive silane bonds. This is illustrated below in Reaction Scheme VI, wherein $R_1$ and $R_2$ are as described herein and $R_3$ is the component to be degradably attached to the particle surface (e.g., a cargo component, as described above). Degradation rates of the resulting conjugates can be tuned by altering the substituents on the Si atom, as detailed previously Reaction Scheme VI

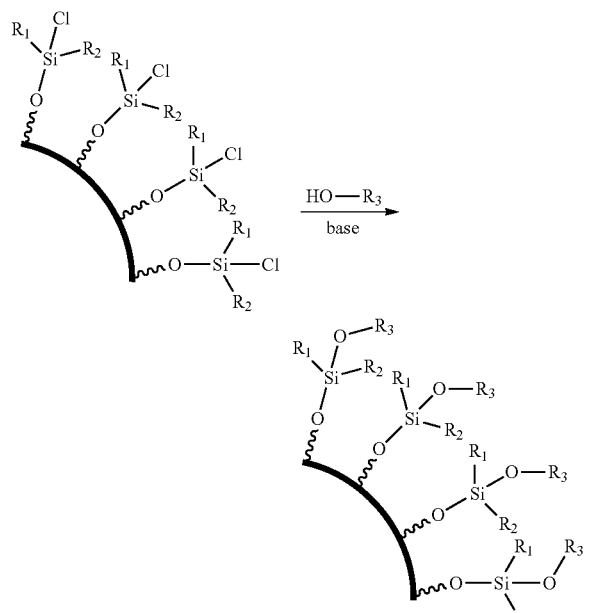

Thus, in certain embodiments, the present invention provides microparticles or nanoparticles having a cargo component degradably attached to a surface thereof, particularly an exposed surface. Specifically, the cargo component may be attached via a pH-sensitive silane bond. The cargo component may be any cargo component described herein. Of course, it is understood that such surface-activation not the only means whereby a cargo component may be associated with a particle according to the invention. Other means for providing a cargo component with a particle in a degradably releasable fashion are also provided herein and are encompassed by the invention.

Compositions according to the pesent invention particularly may be described as encompassing prodrugs that may include one or more labile compounds, as described herein. Thus, the invention may provide prodrug protein, polymer, and particle conjugates having labile silane linkages.

By way of example, the anthracyclines, like doxorubicin (adriamycin) and daunorubicin (illustrated below in Formula (17), constitute a very important class of antineoplastic agents used for many years in the treatment of leukemia, breast carcinoma and other solid tumors; however, their clinical application has been limited by their toxic, dose-related side effects, such as myelosuppression, gastrointestinal disorders, stomatitis, cumulative cardiotoxicity and extravasation. These side-effects may be linked to the pharmacokinetic properties of the anthracycline drugs. Indeed, the anthracycline drugs have a short half-life in the bloodstream and rapidly diffuse throughout the tissues, which results in an even distribution of the drug throughout the body, hence both the malignant and the normal tissues are affected.

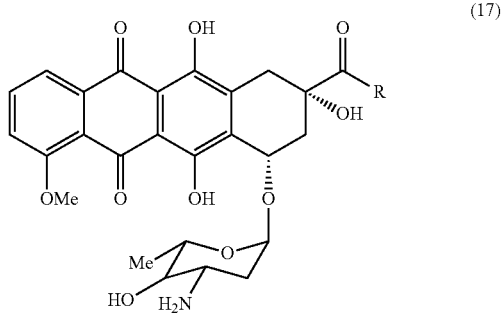

(17)

1: R = CH$_2$OH, doxorubicin
2: R = CH$_3$, daunorubicin

Drug delivery systems have been designed to improve the therapeutic index of the anthracycline drugs by targeting the tumor with greater specificity. The delivery systems consist of the drug attached, via a particular linker or 'spacer', to a carrier that will bind to its specific receptor present on the cancer cell, and thereby direct the whole conjugate to the site of action of the drug. A number of bifunctional spacers include a maleimide functionality that allows linkage of the anthracycline drug to these carriers (see the structures of Formulas (18) and (19), respectively).

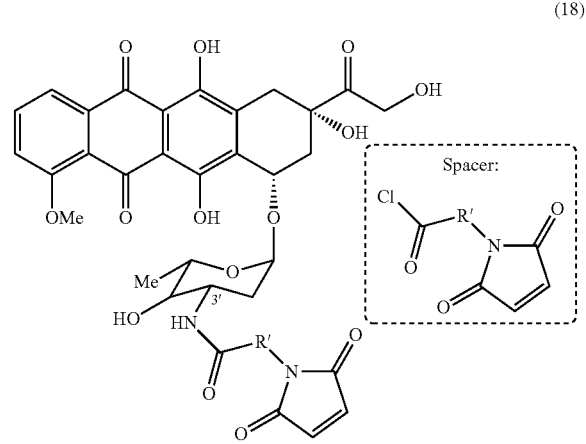

(18)

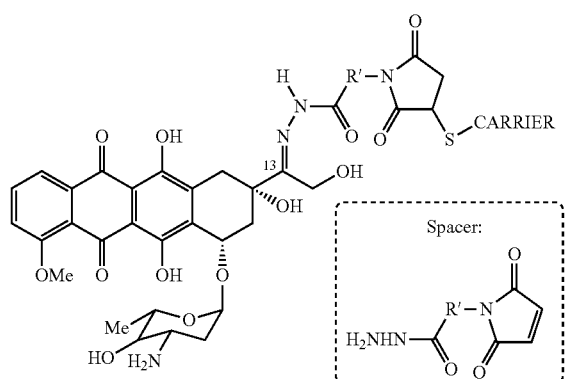

(19)

R' = aliphatic chain or aromatic ring

Initial bioconjugation studies included monoclonal antibodies as carriers. Synthetic polymers were then used as a means to deliver the drug to malignant tissue. As the physiology of tumors was better understood and more overexpressed receptors were found on the cancerous cells, researchers went on to investigate various other carriers such as serum proteins and peptides for which specific receptors were found on the cancer cell, in order to further improve the specificity and efficacy of the anthracycline conjugates.

Alternative approaches for linking the drug to the spacer were also investigated. Although the hydrazone bond was found to be particularly effective to release the anthracycline drug from a number of conjugates, it is not directly applicable to other anticancer drugs.

An approach based on the maleimide chemistry discussed above can be used to create novel, silane-based, pH-sensitive drug-conjugates for a wide range of pharmacologically-relevant molecules. Synthesis of a generic silane-based linker can be carried out using dialkyldicholorosilanes and hydroxy-terminated maleimide derivatives (as shown below in Reaction Scheme VII).

Reaction Scheme VII

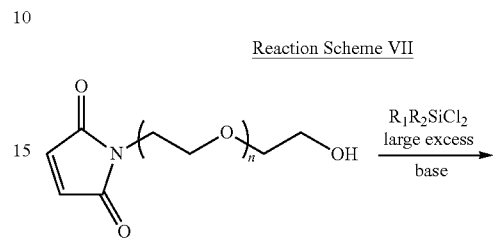

This chloro-silane-based linker can then be conjugated to any pharmacologically-relevant molecule that contains a hydroxy group. For example, Reaction Scheme VIII illustrates synthesis of a pro-drug conjugate of doxorubicin, and Reaction Scheme IX illustrates synthesis of a pro-drug conjugate of docetaxel.

Reaction Scheme VIII

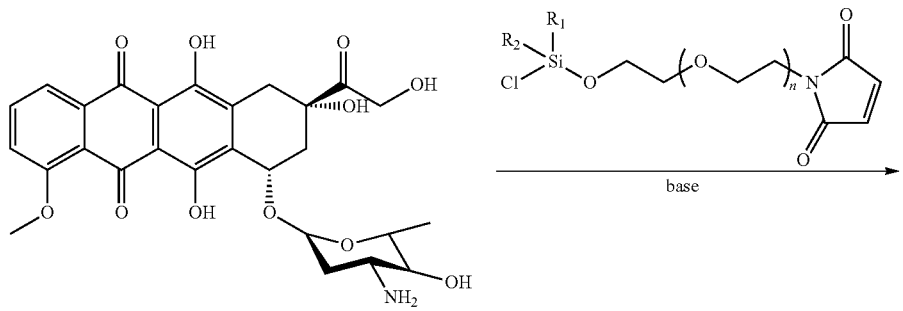

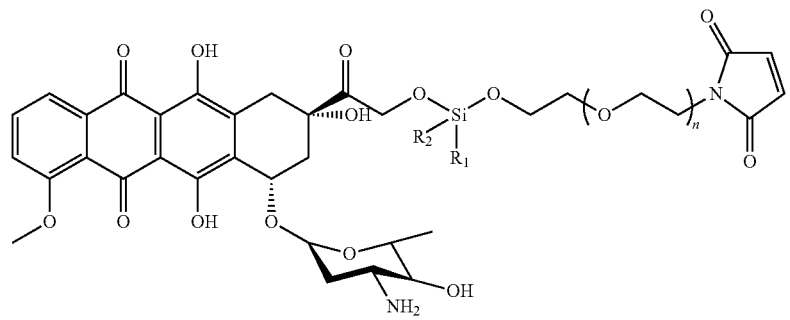

Reaction Scheme IX

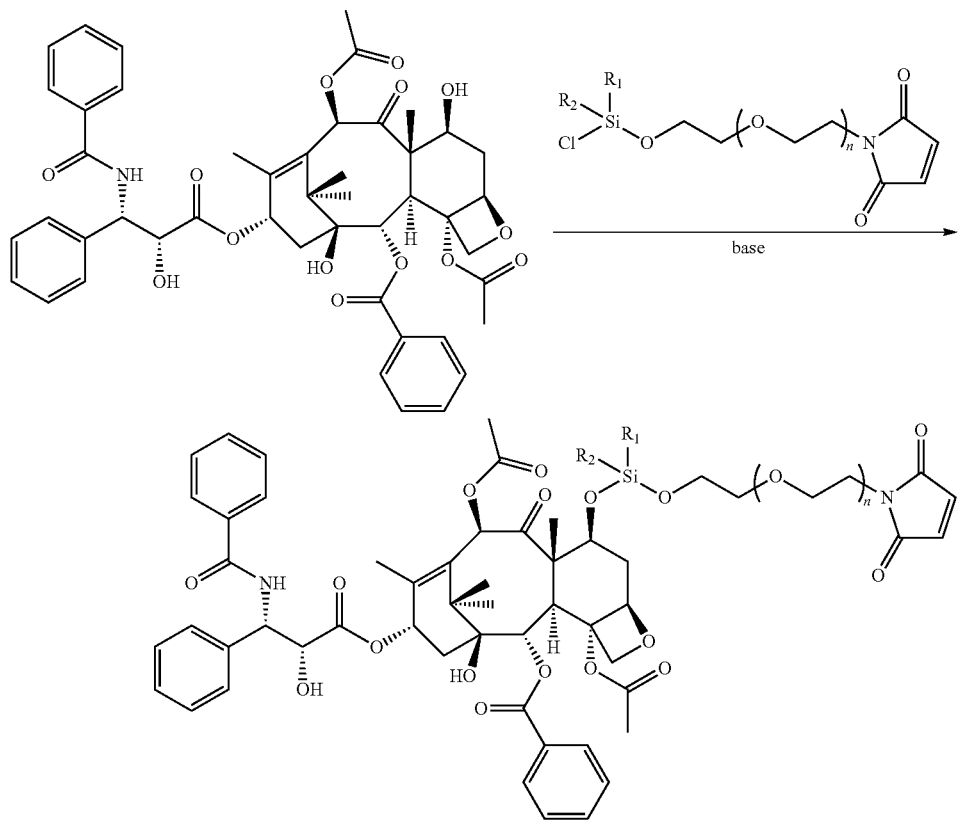

Both pro-drugs from Reactions Schemes VIII and IX contain pH-sensitive, silane linkages and maleimide groups for attachment to sulfhydryl-containing carriers. Once formed, this conjugate can be attached to carrier proteins or any other sulfhydryl-containing moiety. For example, Reaction Scheme X illustrates conjugation of pH-sensitive, Doxorubicin-maleimide conjugate to a sulfhydryl-containing carrier, and Reaction Scheme XI illustrates conjugation of pH-sensitive, Docetaxel-maleimide conjugate to a sulfhydryl-containing carrier.

Reaction Scheme X

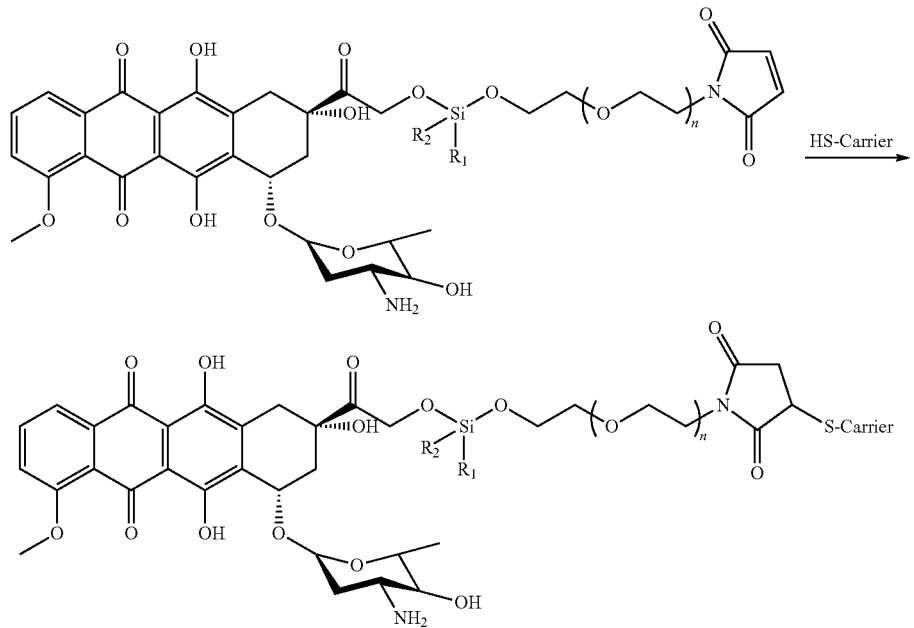

Reaction Scheme XI

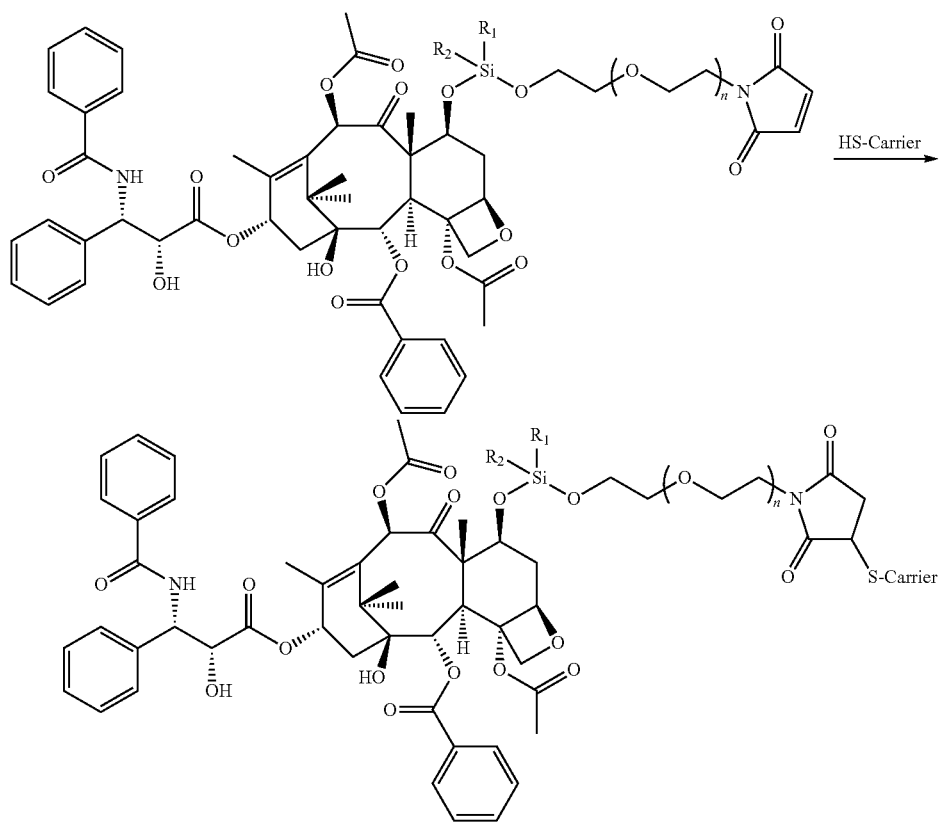

Substituents on Si can be varied in order to affect the degradation rate of the conjugate as discussed previously in the case of silane-based cross-linking agents. The length of PEG spacer needed between the maleimide and silyl group to achieve the maximum release profile will be dictated by both the hydrophobicity of the drug being linked and steric considerations. Extended PEG chains may be necessary to help solubilize poorly water soluble drugs such as docetaxel. A relatively short spacer may create steric constraints in the degradation of the silane. Nucleophilic species other than hydroxyl groups present in the drug molecule, such as the primary amine in doxorubicin, could result in linkages other than Si—O—R; however, these linkages are expected to exhibit pH dependent behavior as well.

In light of the above, it is clear that the invention further comprises a variety of prodrugs, which can comprise any drug having a moiety that will react with the silane compound according to the invention. In specific embodiments, a prodrug according to the invention may have the following structure of Formula (20)

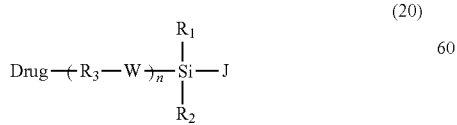

(20)

wherein W, $R_1$, $R_2$, $R_3$, and n are as described herein, is J is a carrier with an optional spacer group included therewith, and the drug is any drug or other cargo component as described above. In specific embodiments, the drug may be any drug having a hydroxyl group thereon.

The carrier J particularly may be a particle, as described herein. Thus, prodrug could be attached to the surface of a micro- or nano-particle formed of a matrix material as described herein. More specifically, the degradable silane group could be attached to a functional group present on the surface of a particle, as described above in relation to Reactions Schemes V and VI.

In one embodiment, the prodrug particularly includes a hydroxy-terminated spacer group attached to the silane group, which specifically may be a hydroxy-terminated maleimide group, as shown in Formula (21) wherein W, $R_1$, $R_2$, $R_3$, and n are as described herein, and the drug is any drug as described above.

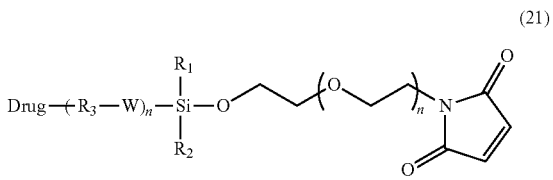

(21)

As shown in Formula (22), the spacer group (e.g., a maleimide group) may be positioned between the silane group and a carrier. In specific embodiments, the carrier may be sulfhydryl containing component (i.e., the carrier may be linked to the spacer via a sulfur linkage). In Formula (22), W, $R_1$, $R_2$, R₃, and n are as described herein, J is a carrier as noted, and the drug is any drug or other cargo component as described above.

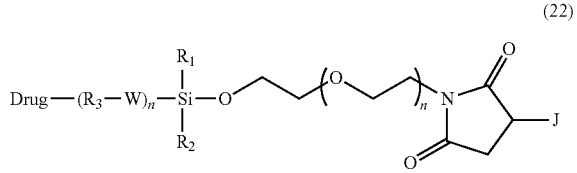

(22)

III. Methods of Treatment

The present invention, in a specific embodiment, provides a variety of methods of treatment. As described above, the present invention provides degradable compounds that may be incorporated into various compositions along with a cargo component, which may be a therapeutic agent (e.g., a drug). Moreover, the ability to form the compositions into discrete particles provides a delivery device for the drug that can be tailored to release the drug only in a desired region or area of the body. Still further, the ability to prepare the particles as nanoparticles even makes possible the specific delivery of drugs (or other cargo components, as described above) to specific cells.

Accordingly, the methods of treatment according to the invention are only limited by the ability to combine a certain drug with a matrix material according to the invention and form it as a discrete particle. As described above, the invention thus allows for a wide variety of treatments.

The methods of the invention comprise administering a composition according to the invention (particularly in the form of discrete particles) to a patient suffering from a condition (or at risk of contracting a condition) that may be prevented, treated, cured, or ameliorated by administration of a cargo component included in the composition. The method may comprise administering the composition in the form of a pharmaceutical composition, as more fully described below.

Since a wide variety of drugs or other therapeutic agents may be combined with a matrix material to form a degradable composition according to the present invention, it follows that the methods of the invention may extend to a wide variety of conditions and diseases. In particular embodiments, the methods of the present invention provide for the treatment, curing, or amelioration of a disease or condition, such as the following: Allergies; Anemia; Anxiety Disorders; Autoimmune Diseases; Back and Neck Injuries; Birth Defects; Blood Disorders; Bone Diseases; Cancers; Circulation Diseases; Dental Conditions; Depressive Disorders; Digestion and Nutrition Disorders; Dissociative Disorders; Ear Conditions; Eating Disorders; Eye Conditions; Foodborne Illnesses; Gastrointestinal Diseases; Genetic Disorders; Heart Diseases; Heat and Sun Related Conditions; Hormonal Disorders; Impulse Control Disorders; Infectious Diseases; Insect Bites and Stings; Institutes; Kidney Diseases; Leukodystrophies; Liver Diseases; Mental Health Disorders; Metabolic Diseases; Mood Disorders; Neurological Disorders; Organizations; Personality Disorders; Phobias; Pregnancy Complications; Prion Diseases; Prostate Diseases; Registries; Respiratory Diseases; Sexual Disorders; Sexually Transmitted Diseases; Skin Conditions; Sleep Disorders; Speech-Language Disorders; Sports Injuries; Thyroid Diseases; Tropical Diseases; Vestibular Disorders; Waterborne Illnesses; and other diseases, such as those listed at the following website: http://www.mic.ki.se/Diseases/Alphalist.html, said disclosure being incorporated herein by reference in its entirety including each reference cited therein.

The invention particularly allows for treatment using combinations of cargo materials, such as two or more different pharmaceuticals. For example, the invention comprises compositions comprising a first particle and at least a second particle. At least one of the first and second particles may comprise a degradable compound as described herein. The first and the second particle may have identical or different formulations and/or structures. For example, the first particle could be formed of a first matrix material and the second particle could be formed of a second matrix material that is different from the first matrix material. In other embodiments, the particles may differ in terms of the degradable compound that is included therewith. The particles particularly may include different cargo components. Of course, it is possible to use three, four, five, or even more particles of differing structure that could be combined in multiple fashions. Of course, it is also recognized that the first particle could refer to a plurality of particles of the first particle type, the second particle could refer to a plurality of particles of the second particle type, and so on.

In this aspect of the invention, it is thus possible to customize cargo delivery. For example, a cancer patient could be given a mixture of cancer drugs that are designed particularly for the type of cancer being treated. A first drug could be included with the first particle (or a plurality of the first particle type), and second drug could be included with the second particle (or a plurality of the second particle type). Likewise, by using the degradable compounds of the invention, it is possible to customize the cargo delivery such that a first cargo component is delivered and released to a first portion of the body, and a second cargo component is delivered and released to a second portion of the body, and so on. Alternatively, the degradable compounds of the invention could be used to customize the time of release of the cargo, such that a first cargo component is delivered and released in a first time frame, and a second cargo component is delivered and released in a second time frame, and so on. Release conditions can be combined to further customize treatment.

IV. Pharmaceutical Formulations

While it is possible for the compositions and/or particles of the present invention to be administered in the raw form, the compositions and/or particles may also be delivered as a pharmaceutical formulation. Accordingly, there are provided by the present invention pharmaceutical formulations comprising a composition a drug or other therapeutic agent that is delivered in association with a degradable or labile compound (e.g., a matrix material comprising a degradable material as described herein, a prodrug as described herein, or a particle with a degradably surface-attached drug as described herein). As such, the formulations may comprise the composition including the drug or other therapeutic agent, as described above.

The inventive compositions and particles can be prepared and delivered with one or more pharmaceutically acceptable carriers therefore, and optionally, other therapeutic agents. Carriers should be acceptable in that they are compatible with any other agents of the formulation and not harmful to the recipient thereof. A carrier may also reduce any undesirable side effects of the agent. Such carriers are known in the art. See, Wang et al. (1980) *J. Parent. Drug Assn.* 34(6):452-462, incorporated by reference in its entirety.

The pharmaceutical formulations may include short-term, rapid-onset, rapid-offset, controlled release, sustained release, delayed release, and pulsatile release formulations, providing the formulations achieve administration of a composition and/or particle as described herein. See *Remington's Pharmaceutical Sciences* (18th ed.; Mack Publishing Company, Eaton, Pa., 1990), herein incorporated by reference in its entirety.

Pharmaceutical formulations for use in the methods of the invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrastemal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) the compositions and/or particles of the invention with a suitable carrier or other adjuvant, which may consist of one or more ingredients. The combination of the compositions and/or particles with the one or more adjuvants is then physically treated to present the formulations in a suitable form for delivery (e.g., shaping into a tablet or forming an aqueous suspension).

Topical formulations may be in any form suitable and readily known in the art for delivery of active agents to the body surface, including dermally, buccally, and sublingually. Typical examples of topical formulations include ointments, creams, gels, pastes, and solutions. Formulations for topical administration in the mouth also include lozenges.

In use, the compositions and/or particles of the presently disclosed subject matter can be used as treatment devices. In such uses, the particle is administered in a therapeutically effective amount to a patient.

EXPERIMENTAL

The present invention will now be described with specific reference to various examples. The following examples are not intended to be limiting of the invention and are rather provided as exemplary embodiments.

Example 1

Synthesis of Acid Labile, Degradable Dimethyl Silane Compound

Hydroxyethyl acetate (HEA) (3.60 g, 31.0 mmol, 4 equiv.) and dichlorodimethyl silane (1.00 g, 7.75 mmol) were added to a flame-dried round-bottom flask equipped with a magnetic stir bar (under argon atmosphere). These were dissolved in 30 mL of dry dichloromethane ($CH_2Cl_2$). After stirring for 5 minutes, triethylamine (5 mL) was added drop wise and allowed to stir for 4 hours at room temperature. The $CH_2Cl_2$ was removed by rotary evaporation in vacuo, and the product was isolated by column chromatography. In particular, the product was eluted using a mixture of hexanes and ethyl acetate (8:2 ratio). Any residual solvent was removed in vacuo to yield a clear and colorless liquid with a yield of 1.36 g (61%). The product having the structure according to Formula (7) was evaluated by 1H NMR (400 MHz, $CDCl_3$) to provide the following: d=0.15 (s, 6H), 3.92 (t, 4H), 4.28 (t, 4H), 5.85 (d, 2H), 6.15 (m, 2H), 6.45 (d, 2H).

EXAMPLE 2

Synthesis of Acid Labile, Degradable Diethyl Silane Compound

Hydroxyethyl acetate (HEA) (2.95 g, 25.5 mmol, 4 equiv.) and dichlorodiethyl silane (1.00 g, 6.36 mmol) were added to a flame-dried round-bottom flask equipped with a magnetic stir bar (under argon atmosphere). These were dissolved in 30 mL of dry dichloromethane ($CH_2Cl_2$). After stirring for 5 minutes, triethylamine (5 mL) was added drop wise and allowed to stir for 4 hours at room temperature. The $CH_2Cl_2$ was removed by rotary evaporation in vacuo, and the product was isolated by column chromatography. In particular, the product was eluted using a mixture of hexanes and ethyl acetate (8:2 ratio). Any residual solvent was removed in vacuo to yield a clear and colorless liquid with a yield of 1.57 g (78%). The product having the structure according to Formula (8) was evaluated by 1H NMR (400 MHz, $CDCl_3$) to provide the following: d=0.63 (t, 4H), 0.96 (d, 6H), 3.94 (t, 4H), 4.23 (t, 4H), 5.82 (d, 2H), 6.15 (m, 2H), 6.43 (d, 2H).

EXAMPLE 3

Synthesis of Acid Labile, Degradable Diisopropyl Silane Compound

Hydroxyethyl acetate (HEA) (2.51 g, 21.6 mmol, 4 equiv.) and dichlorodiethyl silane (1.00 g, 5.40 mmol) were added to a flame-dried round-bottom flask equipped with a magnetic stir bar (under argon atmosphere). These were dissolved in 30 mL of dry dichloromethane ($CH_2Cl_2$). After stirring for 5 minutes, triethylamine (5 mL) was added drop wise and allowed to stir for 4 hours at room temperature. The $CH_2Cl_2$ was removed by rotary evaporation in vacuo, and the product was isolated by column chromatography. In particular, the product was eluted using a mixture of hexanes and ethyl acetate (8:2 ratio). Any residual solvent was removed in vacuo to yield a clear and colorless liquid with a yield of 1.36 g (73%). The product having the structure according to Formula (9) was evaluated by 1H NMR (400 MHz, $CDCl_3$) to provide the following: d=1.05 (s, 4H), 3.96 (t, 4H), 4.28 (t, 4H), 5.83 (d, 2H), 6.14 (m, 2H), 6.42 (d, 2H).

EXAMPLE 4

Synthesis of Acid Labile, Degradable Octa-ethylene Glycol Diethyl Silyl Ether (PEG-8-DES) Compound Tetra-ethylene glycol mono acrylate (TEGMA) (2.10 g, 8.45 mmol, 2.2 equiv.) and dichlorodiethyl silane (0.604 g, 3.84 mmol) were added to a flame-dried round-bottom flask equipped with a magnetic stir bar (under argon atmosphere). These were dissolved in 25 mL of dry dichloromethane ($CH_2Cl_2$). After stirring for 5 minutes, triethylamine (5 mL) was added drop wise and allowed to stir for 4 hours at 0° C. The $CH_2Cl_2$ was removed by rotary evaporation in vacuo, and the product was isolated by column chromatography. In particular, the product was eluted using ethyl acetate. Any residual solvent was removed in vacuo to yield a clear and colorless liquid with a yield of 1.67 g (74%). The product having the structure according to Formula (10) was evaluated by 1H NMR (400 MHz, $CDCl_3$) to provide the following:

d=10.65 (quart., 4H), 1.00 (t, 6H), 3.59 (t, 4H), 3.65 (s, 16H), 3.75 (m, 4H), 3.83 (t, 4H), 4.33 (t, 4H), 5.86 (d, 2H), 6.17 (m, 2H), 6.42 (d, 2H).

EXAMPLE 5

Synthesis of Acid Labile, Degradable Octa-ethylene Glycol Diisopropyl Silyl Ether (PEG-8-DIS) Compound Tetra-ethylene glycol mono acrylate (TEGMA) (2.00 g, 8.06 mmol, 2.5 equiv.) and dichlorodiisopropyl silane (0.597 g, 3.22 mmol) were added to a flame-dried round-bottom flask equipped with a magnetic stir bar (under argon atmosphere). These were dissolved in 25 mL of dry dichloromethane ($CH_2Cl_2$). After stirring for 5 minutes, triethylamine (5 mL) was added drop wise and allowed to stir for 4 hours at 0° C. The $CH_2Cl_2$ was removed by rotary evaporation in vacuo, and the product was isolated by column chromatography. In particular, the product was eluted using ethyl acetate. Any residual solvent was removed in vacuo to yield a clear and colorless liquid with a yield of 1.57 g (80%). The product having the structure according to Formula (11) was evaluated by 1H NMR (400 MHz, $CDCl_3$) to provide the following: d=1.00 (quart, 14H), 1.00 (t, 6H), 3.58 (t, 4H), 3.63 (s, 16H), 3.75 (m, 4H), 3.87 (t, 4H), 4.30 (t, 4H), 5.84 (d, 2H), 6.15 (m, 2H), 6.42 (d, 2H).

EXAMPLE 6

Particles Comprising Degradable Compounds

The degradable compounds prepared in Examples 1-5 were used as crosslinkers to form 5 μm particles, as shown in FIG. 1. The particles essentially were cube shaped (thus having a 2-dimensional square shape as seen in FIG. 1). Particles containing 20%, 40%, 60%, and 80% by weight of each crosslinker were prepared and used to determine optimal release characteristics. The particles also contained dimethylamino ethyl acrylate (DMAEA) as a co-monomer, 2,2-diethoxyacetophenone (DEAP) as a photoinitiator, and rhodamine-B fluorescent dye, which was used as a non-toxic drug mimic. Each particle was degraded at 37° C. in either pH 5.0 buffer (used to show effects at endosomal pH) or pH 7.4 buffer (used to show effects at normal physiologic pH). The release of entrapped rhodamine-B was monitored by UV spectrometer at a wavelength of 552 nm. The release profile for each crosslinker (the compounds of Formulas (7)-(11)) is shown in FIG. 2 through FIG. 6, respectively.

The relative rates of release of rhodamine-B under endosomal pH are as follows DMS>>PEG-8-DES≥DES>>PEG-8-DIS≥DIS. According to this embodiment of the invention, DES and PEG-8-DES were found to provide ideal release rates for release of cargo under endosomal pH conditions. The DMS compound provided a more rapid degradation (i.e., a rapid-release formulation), and the DIS compound provided a more delayed degradation, which may be useful for delayed-release or long acting formulations.

The PEG-8-DES crosslinker further was used to form 200 nm particles as shown in FIG. 7 using 98% by weight PEG-8-DES and 2% by weight DEAP. It is apparent from FIG. 7 that this material led to particles that were homogenous, non-disperse, and small enough for systemic delivery in vivo.

The PEG-8-DES crosslinker also was used to form particles with a comonomer and a cargo component, as shown in FIG. 8. In particular, 200 nm particles were formed using 70% by weight PEG-8-DES, 24% by weight aminopropyl methacrylamide (APMAM) as a co-monomer and to introduce a positive charge, 1% by weight DEAP, and 5% by weight docetaxel.

Particles formed and illustrated in FIG. 8 were degraded at 37° C. in pH 5.0 buffer (endosomal pH) and pH 7.4 buffer (physiologic pH). The 200 nm particles that were dispersed in pH 5.0 degraded and dissolved within two hours, while the same particles suspended in pH 7.4 remained dispersed for 24 hours. This illustrates the pH sensitivity of the inventive, degradable compounds. Thus, particles according to this embodiment of the invention could be administered and expected to remain in particulate form while encountering normal physiologic pH conditions but degrade (and release the drug) at endosomal pH.

Particle toxicity was tested using a cervical cancer cell line (HeLa) by way of in vitro analysis. The results of a MTS assay are shown in FIG. 9. The assay was performed with a particle composition containing docetaxel ("Doc Particles"), and a control composition without docetaxel ("Control"). The MTS assay demonstrated a significant difference in cell viability (or toxicity) between the control particles and the drug loaded particles. The therapeutic effect of the docetaxel loaded particles was substantial, and closely compared with the cell viability of cells dosed with free docetaxel ("Free Doc"). The Control particles were formed of 79% by weight PEG-8-DES, 20% by weight APMAM, and 1% by weight DEAP. The Doc Particles were formed of 72.5% by weight PEG-8-DES, 20% by weight APMAM, 1% by weight DEAP, and 6.5% by weight docetaxel. As can be seen in FIG. 9, the particles without docetaxel essentially had no effect on cell viability. The particles including docetaxel, however, showed a marked decrease in cell viability that approached the cell viability seen when dosing with docetaxel alone. This indicates that the particles effectively were degrading and releasing the bound drug.

Similar encapsulation techniques may be used with other chemotherapeutics, such as paclitaxel, camptothecin, and gemcitabine, as well as other pharmaceuticals. Further, it is possible to use a mixture of particles containing a combination of two or three drugs (two or more drugs combined in the same particles or individual drugs in individual particles).

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the invention. Although specific terms are employed herein, they are used in a generic and descriptive sense only and not for purposes of limitation.

That which is claimed:
1. A molded particle comprising,
   at least 20% of a degradable compound of Formula (3),

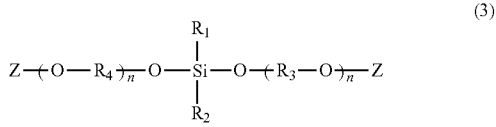

wherein:
R$_1$ and R$_2$ are each independently selected from the group consisting of ethyl, methyl, propyl, isopropyl, butyl, and tert-butyl;

$R_3$ and $R_4$ are each independently selected from the group consisting of —CH$_2$—, —C$_2$H$_4$— and —C$_3$H$_6$—;

each Z is an acrylate group; and n is an integer from 0 to 30;

wherein the compound degrades under physiological conditions; and a biodegradable polymer matrix, wherein the degradable compound crosslinks the biodegradable polymer of the matrix;

wherein the molded particle is stable for more than 24 hours upon exposure to a pH of 7.4 or higher and is degradable in less than 2 hours upon exposure to a pH of 5.0 or lower.

2. The particle of claim 1, wherein the largest dimension of the particle has a size of less than about 500 μm.

3. The particle of claim 1, wherein the largest dimension of the particle has a size of less than about 50 μm.

4. The particle of claim 1, further comprising a cargo component associated with the particle.

5. A pharmaceutical formulation comprising, the particle of claim 1 and a pharmaceutically acceptable carrier.

6. A method of treatment comprising administering to a patient the pharmaceutical composition of claim 5.

7. A composition comprising a first molded particle type and a second molded particle type, wherein the matrix material of at least one particle type comprises i. a degradable compound having the structure of Formula (3),

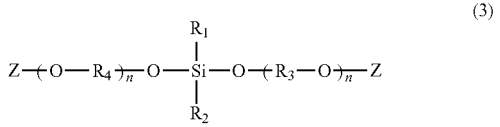

wherein:

$R_1$ and $R_2$ are each independently selected from the group consisting of ethyl, methyl, propyl, isopropyl, butyl, and tert-butyl;

$R_3$ and $R_4$ are each independently selected from the group consisting of —CH$_2$—, —C$_2$H$_4$— and —C$_3$H$_6$—;

each Z is an acrylate group; and n is an integer from 0 to 30;

wherein the compound degrades under physiological conditions; and ii. a biodegradable polymer matrix, wherein the degradable compound crosslinks the biodegradable polymer of the matrix;

wherein the at least one particle type is stable for more than 24 hours upon exposure to a pH of 7.4 or higher and is degradable in less than 2 hours upon exposure to a pH of 5.0 or lower, and wherein, the first particle type is different from the second particle type.

8. A medical device for delivering a cargo, said device comprising a particle of claim 1.

9. The device of claim 8, wherein said device is selected from the group consisting of a particle, stent, catheter and implant.

10. The device of claim 8, wherein said device is degradable.

11. The particle of claim 1, wherein said matrix comprises at least one biodegradable polymer selected from the group consisting of a polyethylene glycol, polyglycolic lactic acid, a polyester, a polyanhydride, a polyamide, a phosphorous-based polymer, a poly(cyanoacrylate), a polyurethane, a polyorthoester, a polydihydropyran, and a polyacetal and combinations thereof.

12. The particle of claim 1, wherein the polymer is selected from the group consisting of a polyethylene glycol, polyglycolic lactic acid, polylactic acid, polyglycolic acid, poly(hydroxybutyrate), poly(ε-caprolactone), poly(β-malic acid), poly(dioxanones), poly(sebacic acid), poly(adipic acid), poly(terpthalic acid), poly(imino carbonates), polyaminoacids, a polyphosphate, a polyphosphonate, and a polyphosphazene and combinations thereof.

13. The particle of claim 1, wherein said matrix comprises at least one biodegradable polymer selected from the group consisting of polyethylene glycol and polyglycolic lactic acid.

14. The particle of claim 1, wherein n is an integer from 1 to 10.

15. The particle of claim 14, wherein said degradable compound is selected from the group consisting of:

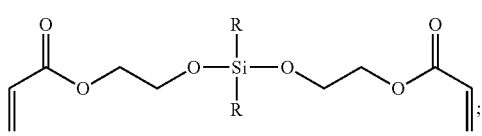

(7)

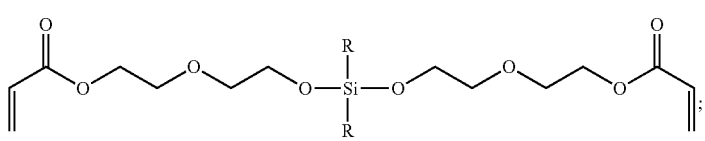

(9)

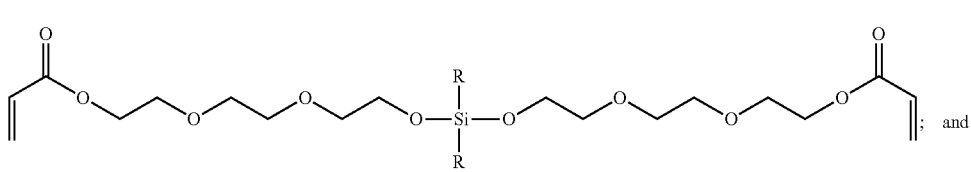

(11)

; and

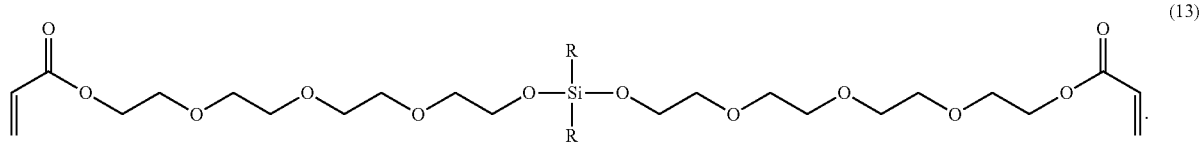

wherein, R is methyl, ethyl, or isopropyl; or combinations of said compounds.

16. The particle of claim 4, wherein said cargo component is selected from the group consisting of biologically active materials, elemental materials, therapeutic agents, diagnostic agents, drugs, genetic materials, nucleotide sequences, amino-acid sequences, ligands, oligopeptides, proteins, vaccines, biologics, DNA, RNA, imaging agents, contrast agents, antisense agents, radiotracers, radiopharmaceuticals, and combinations thereof.

17. The particle of claim 1, wherein said polymer matrix comprises a co-polymer.

18. The particle of claim 4, wherein less than about 20% of said cargo is released from said particle within about 24 hours upon exposure to a pH of 7.4 or above.

19. The particle of claim 4, wherein at least 20% of said cargo is released from said particle within about 2 hours upon exposure to a pH of 5.0 or below.

20. The particle of claim 16, wherein said cargo component is a drug selected from one or more anticancer agents.

21. The particle of claim 4, wherein said degradable compound is PEG-8-DIS.

22. The particle of claim 4, wherein said particle is comprised of at least 40% of said degradable compound.

23. The particle of claim 4, wherein said particle is comprised of at least 60% of said degradable compound.

24. The particle of claim 4, wherein said particle is comprised of at least 80% of said degradable compound.

* * * * *